United States Patent
Atabekov et al.

(10) Patent No.: US 8,192,984 B2
(45) Date of Patent: Jun. 5, 2012

(54) CREATION OF ARTIFICIAL INTERNAL RIBOSOME ENTRY SITE (IRES) ELEMENTS

(75) Inventors: Joseph Atabekov, Moscow (RU); Yurii Dorokhov, Moscow (RU); Maxim Skulachev, Moscow (RU); Peter Ivanov, Moscow (RU); Yuri Gleba, Halle/Saale (DE)

(73) Assignee: Icon Genetics, Inc., Princeton, NJ (US)

( * ) Notice: Subject to any disclaimer, the term of this patent is extended or adjusted under 35 U.S.C. 154(b) by 1137 days.

(21) Appl. No.: 10/489,221

(22) PCT Filed: Sep. 3, 2002

(86) PCT No.: PCT/EP02/09843
§ 371 (c)(1),
(2), (4) Date: Oct. 8, 2004

(87) PCT Pub. No.: WO03/020927
PCT Pub. Date: Mar. 13, 2003

(65) Prior Publication Data
US 2005/0059004 A1  Mar. 17, 2005

(30) Foreign Application Priority Data
Sep. 4, 2001 (DE) .................................. 101 43 237

(51) Int. Cl.
C12N 15/00 (2006.01)
C12N 15/09 (2006.01)
C12N 15/11 (2006.01)
C12N 15/67 (2006.01)

(52) U.S. Cl. .................... 435/320.1; 435/325; 435/410; 435/243; 536/23.1; 536/24.1

(58) Field of Classification Search .................. None
See application file for complete search history.

(56) References Cited

U.S. PATENT DOCUMENTS

| | | | |
|---|---|---|---|
| 5,139,812 A | 8/1992 | Lebacq | |
| 5,474,925 A | 12/1995 | Maliyakal et al. | |
| 5,576,198 A | 11/1996 | McBride et al. | |
| 5,627,059 A | 5/1997 | Capecchi et al. | |
| 5,670,623 A | 9/1997 | Shoseyov et al. | |
| 5,723,765 A | 3/1998 | Oliver et al. | |
| 5,877,402 A | 3/1999 | Maliga et al. | |
| 5,910,628 A * | 6/1999 | Miller et al. | 800/278 |
| 6,100,448 A | 8/2000 | Thompson et al. | |
| 6,146,845 A * | 11/2000 | Kikly et al. | 435/69.1 |
| 6,147,278 A | 11/2000 | Rogers et al. | |
| 6,174,700 B1 | 1/2001 | Haynes et al. | |
| 6,300,545 B1 | 10/2001 | Baszczynski et al. | |
| 6,331,416 B1 | 12/2001 | Shani et al. | |
| 6,331,661 B1 | 12/2001 | Baszczynski et al. | |
| 6,376,745 B1 | 4/2002 | Atabekov et al. | |
| 6,781,033 B2 | 8/2004 | Staub et al. | |
| 6,833,254 B2 * | 12/2004 | Dasgupta et al. | 435/69.1 |
| 2003/0049228 A1 | 3/2003 | Santa-Cruz et al. | |
| 2003/0188337 A1 | 10/2003 | Day et al. | |
| 2004/0055037 A1 | 3/2004 | Gleba et al. | |
| 2004/0083499 A1 | 4/2004 | Eibl et al. | |
| 2004/0088764 A1 | 5/2004 | Gleba et al. | |
| 2004/0137631 A1 | 7/2004 | Herz et al. | |
| 2004/0191788 A1 | 9/2004 | Gleba et al. | |
| 2004/0221330 A1 | 11/2004 | Klimyuck et al. | |
| 2004/0244073 A1 | 12/2004 | Klimyuck et al. | |
| 2004/0255347 A1 | 12/2004 | Klimyuck et al. | |
| 2005/0014150 A1 | 1/2005 | Atabekov et al. | |
| 2005/0015829 A1 | 1/2005 | Koop et al. | |
| 2005/0015830 A1 | 1/2005 | Dorokhov et al. | |
| 2005/0059004 A1 | 3/2005 | Atabekov et al. | |
| 2005/0066384 A1 | 3/2005 | Klimyuck et al. | |
| 2005/0091706 A1 | 4/2005 | Klimyuck et al. | |
| 2006/0253924 A1 * | 11/2006 | Turk et al. | 800/279 |

FOREIGN PATENT DOCUMENTS

| | | |
|---|---|---|
| EP | 0270 248 | 6/1988 |
| EP | 1 045 037 | 10/2000 |
| WO | WO 87/00551 | 1/1987 |
| WO | WO 94/16089 | 7/1994 |
| WO | WO 95/34668 | 12/1995 |
| WO | WO 96/17954 | 6/1996 |
| WO | WO 98/09505 | 3/1998 |
| WO | WO 98/44097 | 10/1998 |
| WO | WO 98/54342 | 12/1998 |
| WO | WO 99/25821 | 5/1999 |
| WO | WO 99/25855 | 5/1999 |
| WO | WO 99/36516 | 7/1999 |
| WO | WO 00/17365 | 3/2000 |
| WO | WO 00/20611 | 4/2000 |
| WO | WO 00/32799 | 6/2000 |

(Continued)

OTHER PUBLICATIONS

Lustig AJ, Petes TD. Long poly(A) tracts in the human genome are associated with the Alu family of repeated elements. J Mol Biol. Dec. 15, 1984;180(3):753-9.*

NCBI Sequence results for GenBank Acc. No. AZ342739, www.ncbi.nlm.nih.gov/entrez/viewer.fcgi?db=nucgss&id=10420275, Sep. 29, 2000, pp. 1-2.*

Product information for *E. coli* K12 ER2420/pBeloBAC11, New England BioLabs Catalog # 4154S. printed Aug. 2, 2007, pp. 1-2.*

NCBI Sequence results for GenBank Acc. No. AQ304254, www.ncbi.nlm.nih.gov/entrez/viewer.fcgi?db=nucgss&id=4021052, Dec. 15, 1999, pp. 1-2.*

(Continued)

*Primary Examiner* — Maria Marvich

(74) *Attorney, Agent, or Firm* — Lerner, David, Littenberg, Krumholz & Mentlik, LLP

(57) ABSTRACT

A method of producing a nucleic acid sequence having an adenine-rich nucleic acid block of at least 25 nucleotides in length is provided. The nucleic acid sequence that is produced is capable of initiating translation at an internal ribosome entry site (IRES) and the adenine-rich nucleic acid block comprises from 40 to 100 mol-% adenine.

14 Claims, 24 Drawing Sheets

FOREIGN PATENT DOCUMENTS

| | | |
|---|---|---|
| WO | WO 00/68391 | 11/2000 |
| WO | WO 00/68431 | 11/2000 |
| WO | WO 00/70019 | 11/2000 |
| WO | WO 00/77174 | 12/2000 |
| WO | WO 00/77175 | 12/2000 |
| WO | WO 00/78985 A1 | 12/2000 |
| WO | WO 01/11020 | 2/2001 |
| WO | WO 01/55369 | 8/2001 |
| WO | WO 01/59138 A2 | 8/2001 |
| WO | WO 01/81600 | 11/2001 |
| WO | WO 02/12522 | 2/2002 |
| WO | WO 02/29068 | 4/2002 |
| WO | WO 02/46438 | 6/2002 |
| WO | WO 02/46440 | 6/2002 |
| WO | WO 02/055651 | 7/2002 |
| WO | WO 02/057466 | 7/2002 |
| WO | WO 02/068664 | 9/2002 |
| WO | WO 02/077246 | 10/2002 |
| WO | WO 02/079481 | 10/2002 |
| WO | WO 02/088369 | 11/2002 |
| WO | WO 02/101060 | 12/2002 |
| WO | WO 03/001900 | 1/2003 |
| WO | WO 03/004658 | 1/2003 |
| WO | WO 03/020927 | 3/2003 |
| WO | WO 03/020928 | 3/2003 |
| WO | WO 03/020938 | 3/2003 |

OTHER PUBLICATIONS

Mahairas GG, Wallace JC, Smith K, Swartzell S, Holzman T, Keller A, Shaker R, Furlong J, Young J, Zhao S, Adams MD, Hood L. 1999. Sequence-tagged connectors: a sequence approach to mapping and scanning the human genome. Proc Natl Acad Sci U S A. Aug. 17, 1999;96(17):9739-44.*
Alberts B, Bray D, Lewis J, Raff M, Roberts K, and Watson J. 1994. Molecular biology of the cell, 3rd Ed. Garland Publ. Inc., New York, pp. 58-59.*
Smith, A. 1997.Oxford Dictionary of Biochemistry and Molecular Biology, Oxford University Press, USA. pp. 34, 131 and 426.*
Fowlks et al, Detection and Sequence of an Internal A-Rich T1 Oligonucleotide Series in Brome Mosaic Viral RNA3, FEBS Letters, Jul. 1981 pp. 32-38.*
Karpova et al, The 3'-untranslated region of brome mosaic virus RNA does not enhance translation of capped mRNAs in vitro, FEBS Letters 360 (1995) 281-285.*
Gaille et al, The tobacco etch viral 5' leader and poly(A) tail are functionally synergistic regulators of translation, Gene, 1995, vol. 165, pp. 233-238.*
Bergamini et al , Picornavirus IRESes and the poly(A) tail jointly promote cap-independent translation in a mammalian cell-free system. RNA 2000 6: 1781-1790.*
Iizuka et al, Cap-Dependent and Cap-Independent Translation by Internal Initiation of mRNAs in Cell Extracts Prepared from *Saccharomyces cerevisiae*, Molecular and Cellular Biology, Nov. 1994, p. 7322-7330.*
Hagemann et al. "Extranuclear Inheritance: Plastid Genetics" *Progress in Botany*, vol. 55, 260-275 (1994).
Klaus et al. "Generation of Marker Free Plastid Transformants Using a Transiently Cointegrated Selection Gene" *Nature Biotechnology* 22: 225-229 (2004).
Mühlbauer et al. "Functional analysis of plastid DNA replication origins in tobacco by targeted inactivation" *The Plant Journal*, 32:175-184 (2002).
Ruf et al. "Stable Genetic Transformation of Tomato Plastids and Expression of a Foreign Protein in Fruit" *Nature Biotechnology* 19: 870-875 (2001).
Shimada et al. "Fine Structural Features of the Chloroplast Genome: Comparison of the Sequenced Chloroplast Genomes" *Nucleic Acids Research* 19: 983-995 (1991).
Shinozaki et al. "The Complete Nucleotide Sequence of the Tobacco Chloroplast Genome: Its Gene Organization and Expression" *The EMBO Journal* 5: 2043-2049 (1986).
Sidorov et al. "Stable Chloroplast Transformation in Potato: Use of Green Fluorescent Protein as a Plastid Marker" *The Plant Journal* 19: 209-216 (1999).
Donson et al. "Systemic expression of a bacterial gene by a tobacco mosaic" *Proc. Natl. Acad. Sci. USA 88*: 7204-7208 (1991).
Murakami et al. "High-level expression of exogenous genes by replication-competent retrovirus vectors with an internal ribosomal entry site" *Gene 202*: 23-29 (1997).
Derbyshire et al. "Lightning strikes twice: Intron-intein coincidence" *Proc. Natl. Acad. Sci. USA 95*:1358-1357 (1998).
Wu et al. "Markerless Deletions of *pil* Genes in *Myxococcus xanthus* generated by Counterselection with the *Bacillus subtilis sacB* Gene" *Journal of Bacteriology 178*(19):5817-5281 (1996).
Attal et al., "The efficiency of different IRESs (Internal Ribosomes Entry Site) in monocistronic mRNAs," *Molecular Biology Reports* 27: 21-26 (2000).
Skulachev et al., "Internal Initiation of Translation Directed by the 5'-Untranslated Region of the *Tobamovirus* Subgenomic RNA $I_2$," *Virology* 263: 139-154 (1999).
Cornelis et al., Molecular Cell, 5; 597-605 (2000).
Martinez-Salas E, Fernãndez-Miragall O. Picornavirus IRES: structure function relationship. Curr Pharm Des.2004;10 (30):3757-67.
Stoneley M, Willis AE. Cellular internal ribosome entry segments: structures, trans-acting factors and regulation of gene expression. Oncogene. Apr. 19, 2004;23(18):3200-7.
Parry et al. Construction of a, bidirectional promoter probe vector and its use in analyzing nod gene expression *Rhizobium loti*. Gene 150: 105-109 (1994).
Sanz et al. Altered local and systemic spread of movement deficient virus in transgenic tobacco plants expressing the cucumber mosaic virus 3a protein Arch Virol.145:2387-2401 (2000).
Altschul et al. "Basic Local Alignment Search Tool," *J. Mol. Biol.*, 215:403-410 (1990).
Arnold et al. "Allelic Ladder D18551 Allele 8" EMBL Database Accession No. AAX01351 (Apr. 14, 1994).
Bagwell et al. "Poly-dA 50mer Probe Target Sequence" EMBL Database Accession No. AAQ66922 (Jan. 24, 1995).
Bergamini et al. "Picornavirus IRESes and the Poly(A) tail Jointly Promote Cap-Independent Translation in a Mammalian Cell-free System," *RNA*, 6:1781-1790 (2000).
Chappell et al. "A 9-nt Segment of Cellular mRNA Can Function as an Internal Ribosome Entry Site (IRES) and When Present in Linked Multiple Copies Greatly Enhances IRES Activity," *PNAS*, 97(4):1536-1541 (Feb. 15, 2000).
Dorokhov et al. "Polypurine (A)-rich Sequences Promote Cross-kingdom Conservation of Internal Ribosome Entry," *PNAS*, 99(8):5301-5306 (Apr. 16, 2002).
Houdebine et al. "Internal Ribosome Entry Sites (IRESs): Reality and Use" *Transgenic Research*, 8:157-177 (1999).
Ivanov et al. "A *Tobamovirus* Genome That Contains an Internal Ribosome Entry Site Functional In Vitro," *Virology*, 232:32-43 (1997).
Martinez-Salas, Encarnacion. "Internal Ribosome Entry Site Biology and Its Use in Expression Vectors," *Current Opinion in Biotechnology*, 10:458-464 (1999).
Owens et al. "Identification of Two Short Internal Ribosome Entry Sites Selected From Libraries of Random Oligonucleotides," *PNAS*, 98(4):1471-1476 (Feb. 13, 2000).
Pearson et al. "Improved Tools for Biological Sequence Comparison," *Proc. Nat'l. Acad. Sci. USA*, 85: 2444-2448 (Apr. 1988).
Preiss et al. "Dual Function of the Messenger RNA Cap Structure in Poly(A)-tail-promoted Translation in Yeast," *Nature*, 392:516-520 (Apr. 2, 1998).
Toth et al. "A Novel Strategy for the Expression of Foreign Genes From Plant Virus Vectors," *FEBS Letters*, 489:215-219 (2001).
Albert et al. (1995) "Site-specific integration of DNA into wild-type and mutant lox sites placed in the plant genome" The Plant Journal 7:649-659.
Allison et al., "Deletion of rpoB Reveals a Second Distinct Transcription System in Plastids of Higher Plants," The EMBO Journal, 15:11 2802-2809 (1996).
Anandalakshmi et al. (1998) "A viral suppressor of gene silencing in plants" Proc. Natl. Acad. Sci. U.S.A. 95:13079-13084.

Anandalakshmi et al. (2000) "A calmodulin-related protein that suppresses posttranscriptional gene silencing in plants" Science 290:142-144.
Bateman et al. (2000) "Tools for chloroplast transformation in *Chlamydomonas*: expression vectors and a new dominant selectable marker" Mol. Gen. Genet. 263:401-410.
Bogorad, Lawrence, "Engineering Chloroplasts: an Alternative Site for Foreign Genes, Proteins, Reactions and Products," TIBTECH, 18:257-263 (Jun. 2000).
Bouchez et al. (1993) "A binary vector based on Basta resistance for in planta transformation of *Arabidopsis thaliana*" C. R. Acad. Sci. Paris, Science de la vie 316:1188-1193.
Boynton et al., "Chloroplast Transformation in *Chlamydomonas* with High Velocity Microprojectiles," Science, 240:1534-1538 (1988).
Carpin et al. (2001) "Identification of a Ca2+-Pectate Binding Site on an Apoplastic Peroxidase" The Plant Cell 13:511-520.
Clelland et al. (1999) "Hiding Messages in DNA Microdots," Nature 399:533-534.
Coutts et al. "Development of Geminivirus-based Gene Vectors for Dicotyledonous Plants" Australian Journal of Plant Physiology 17:365-375 (1990).
Dale et al. "Intra- and intermolecular site-specific recombination in plant cells mediated by bacteriophage P1 recombinase" Gene 91:79-85 (1990).
Dale et al. "Mutations in the CRE/LOX Recombination Site Enhance the Stability of Recombination Products: Applications for Gene Targeting in Plants" Journal of Cellular Biochemistry 50 (S16S):206 (1992).
Daniell, "New Tools for Chloroplast Genetic Engineering," Nature Biotechnology, 17:855-856 (Sep. 1999).
De Santis-Maciossek et al., "Targeted Disruption of the Plastid RNA Polymerase Genes rpoA, B and C1: Molecular Biology, Biochemistry and Ultrastructure," The Plant Journal, 18(5):477-489 (1999).
Domingo et al. (1999) "Identification of a novel peptide motif that mediates cross-linking of proteins to cell walls" The Plant Journal 20:563-570.
Drescher et al., "The Two Largest Chloroplast Genome-Encoded Open Reading Frames of Higher Plants are Essential Genes," The Plant Journal, 22(2):97-104 (2000).
El-Sheekh, M.M. (2000) "Stable Chloroplast Transformation in *Chlamydomonas reinhardtii* using Microprojectile Bombardment" Folia Microbiol. 45(6) 496-504.
Fischer et al., "Selectable Marker Recycling in the Chloroplast," Mol. Gen. Genet., 251:373-380 (1996).
Gatz et al. (1991) "Regulation of a modified CaMV 35S promoter by the Tn10-encoded Tet repressor in transgenic tobacco" Mol. Gen. Genet. 227:229-237.
Hager et al., "Enslaved Bacteria as New Hope for Plant Biotechnologists," Appl. Microbiol. Biotechnol., 54:302-310 (2000).
Heifetz, Peter B., "Genetic Engineering of the Chloroplast," Biochimie, 82:655-666 (2000).
Hoff et al. (2001) "A recombinase-mediated transcriptional induction system in transgenic plants" Plant Mol. Biol. 45:41-49.
Horvath et al., "Targeted Inactivation of the Plastid ndhB Gene in Tobacco Results in an Enhanced Sensitivity of Photosynthesis to Moderate Stomatal Closure," Plant Physiology, 123:1337-1349 (Aug. 2000).
Iamtham et al. (2000) "Removal of antibiotic resistance genes from transgenic tobacco plastids" 18:1172-1176.
Jeon et al. (2000) "T-DNA insertional mutagenesis for functional genomics in rice" Plant J. 22:561-570.
Kofer et al., "PEG-Mediated Plastid Transformation in Higher Plants," In Vitro Cell. Dev. Biol.—Plant, 31:303-309 (1998).
Koshinsky et al. (2000) "Cre-lox site-specific recombination between *Arabidopsis* and tobacco chromosomes" The Plant Journal 23:715-722.
Kozak, "Initiation of Translation in Prokaryotes and Eukaryotes" Gene 234:187-208 (1999).
Kumagai et al. (1995) "Cytoplasmic inhibition of carotenoid biosynthesis with virus-derived DNA" Proc. Natl. Acad. Sci. USA 92:1679-1683.

Lehtiö et al. (2001) "Directed immobilization of recombinant staphylococci on cotton fibers by functional display of a fungal cellulose-binding domain" FEMS Microbiology Letters 195:197-204.
Lopez de Quinto et al. "Parameters Influencing Translational Efficiency in Aphthovirus IRES-Based Bicistronic Expression Vectors" Gene 217:51-56 (1998).
Matzk et al. (1994) "Improved Techniques for haploid Production in Wheat using Chromosome Elimination" Plant Breeding 113:125-129.
Melchers et al (1974) "Somatic Hybridisation of Plants by Fusion of Protoplasts" Molec. Gen. Genet. 135:277-294.
Michael et al. (1999) "Efficient gene-specific expression of Cre recombinase in the mouse embryo by targeted insertion of a novel IRES-Cre cassette into endogenous loci" Mech. Dev. 85:35-47.
Mizuguchi et al. (2000) "IRES-Dependent Second Gene Expression is Significantly Lower Than Cap-Dependent First Gene Expression in a Bicistronic Vector" Mol. Ther. 1:376-382.
Monde et al., "Post-Transcriptional Defects in Tobacco Chloroplast Mutants Lacking the Cytochrome b6/f Complex," The Plant Journal, 21(1):61-72 (2000).
Mountford et al. (1995) "Internal ribosome entry sites and dicistronic RNAs in mammalian transgenesis" Trends Genet. 11:179-184.
Niepel et al. (1999) "Identification and Characterization of the Functional Elements within the Tobacco Etch Virus 5' Leader Required for Cap-Independent Translation" J. Virol. 73:9080-9088.
Neunzig et al. "Self replicating vectors as a tool for gene targeting in plants" Experienta 46:A34 (1990).
Peterson-Burch et al. "Retroviruses in plants?" Trends in Genetics 16:151-152 (2000).
Porta et al. "Use of Viral Replicons for the Expression of Genes in Plants" Molecular Biotechnology 5:209-221 (1996).
Qin et al. (Mar. 1994) "Cre recombinase-mediated site-specific recombination between plant chromosomes" Proc. Natl. Acad. Sci. 91:1706-1710.
Riera-Lizarazu et al. (1993) "Polyhaploid Production in the Triticeae: Wheat x Tripsacum Crosses" Crop Science 33:973-976.
Ruf et al., "Targeted Inactivation of a Tobacco Intron-Containing Open Reading Frame Reveals a Novel Chloroplast-Encoded Photosystem I-Related Gene," The Journal of Cell Biology, 139(1):95-102 (Oct. 6, 1997).
Schreuder et al. (1993) "Targeting of a Heterologous Protein to the Cell Wall of *Saccharomyces cerevisiae*" Yeast 9:399-409.
Serino et al., "RNA Polymerase Subunits Encoded by the Plastid rpo Genes are Not Shared with the Nucleus-Encoded Plastid Enzyme," Plant Physiol., 117:1165-1170 (1998).
Shepard et al. (1983) "Genetic Transfer in Plants Through Interspecific Protoplast Fusion" Science 219:683-688.
Stanley, J. "Geminiviruses: plant viral vectors" Current Opinion in Genetics and Development 3:91-96 (1993).
Staub et al. (1994) "Extrachromosomal elements in tobacco plastids" Proc. Natl. Acad. Sci. 91:7468-7472.
Staub et al., "Expression of a Chimeric uidA Gene Indicates that Polycistronic mRNAs are Efficiently Translated in Tobacco Plastids," The Plant Journal, 7(5):845-848 (1995).
Suzuki et al. (1997) "Generation and maintenance of tandemly repeated extrachromosomal plasmid DNA in *Chlamydomonas* chloroplasts" Plant J. 11:635-648.
Suzuki et al., "Engineering of the rp123 Gene Cluster to Replace the Plastid RNA Polymerase α Subunit with the *Escherichia coli* Homologue," Curr. Genet., 38:218-225 (2000).
Ueda et al. (2000) "Genetic immobilization of proteins on the yeast cell surface" Biotechnology Advances 18:121-140.
Urwin et al. (2000) "Functional characterization of the EMCV IRES in plants" Plant J. 24:583-589.
Valancius et al. (1991) "Testing an "In-Out" Targeting Procedure for Making Subtle Genomic Modifications in Mouse Embryonic Stem Cells" Molecular and Cellular Biology 11:1402-1408.

Van Haaren et al. (1993) "Prospects of applying a combination of DNA transposition and site-specific recombination in plants: a strategy for gene identification and cloning" Plant Molecular Biology 23:525-533.

Vergunst et al. "Cre/lox-mediated site-specific integration of *Agrobacterium* T-DNA in *Arabidopsis thaliana* by transient expression of cre" Plant Molecular Biology 38:393-406 (1998).

Walden et al. "Gene-transfer and plant regeneration techniques" Trends in Biotechnology 13:324-331 (1995).

Wells et al. (1999) "Codon optimization, genetic insulation, and rtTA reporter improve performance of the tetracycline switch" Transgenic Res. 8:371-381.

Whitney et al., "Directed Mutation of the Rubisco Large Subunit of Tobacco Influences Photorespiration and Growth," Plant Physiology, 121:579-588 (Oct. 1999).

Wilde et al. (1992) "Control of gene expression in tobacco cells using a bacterial operator-repressor system" EMBO J. 11:1251-1259.

Zhao et al. "Development and evaluation of a complementation-dependent gene delivery system based on cucumber mosaic virus" Arch Virol 145:2285-2295 (2000).

* cited by examiner

EMCV IRES-containing mRNA 5'UTR (SEQ ID NO:1):

```
ttgaaagccg ggggtgggag atccggattg ccagtctact cgatatcgca ggctgggtcc  60
gtgactaccc actcctactt tcaacgtgaa ggctacgata gtgccagggc gggtactgcc 120
gtaagtgcca ccccaaccaa caaaacaaaa accccccccc cccccccccc cccccccccc 180
cccccccccc cccccccccc cccccccccc cccccccccc cccccccccc cccccccccc 240
cccccccccc cccccccccc ccccccccca acgttactgg ccgaagccgc ttggaataag 300
gccggtgtgc gtttgtctat atgttatttc taccacatca ccgtctttg gtggtgtgag 360
ggcccggaac ctggccctgt cttcttgacg agcattccta ggggtctttc ccctctcgcc 420
aaaggaatgt aaggtctgtt gaatgtcgtg aaggaagcag ttcctctgga agcttcttga 480
agacaagcaa cgtctgtagc gacccttgc aggcagcgga aatccccacc tggtaacagg 540
tgcctctgcg gccaaaagcc acgtgtataa gatacacctg caaggcggc acaaccccag 600
tgccacgttg tgagttggat agttgtgaa agagtcaaat ggctcacctc aagcgtattc 680
aacaaggggc tgaaggatgc ccagaaggta ccccattgta tgggatctga tctgggcct 740
cggtgcacgt gctctacacg tgttgagtcg aggttaaaaa acgtctaggc ccccgaacc 820
acggggacgt ggttttcctt tgaaaaccac gattgtaaga tggctacaac tatggaacaa 880
gagatttgtg cgcattccct cacgtttaaa ggatgcccga a ATG
```

Poliovirus IRES-containing mRNA 5'UTR (SEQ ID NO:2):

```
ttaaaacagc tctggggttg ttcccacccc agaggcccac gtggcggcta gtacactggt  60
atcacggtac ctttgtacgc ctgttttata ctccctcccc cgcaacttag aagcatacaa 120
ttcaagctca ataggagggg gtgcaagcca gcgcctccgt gggcaagcac tactgtttcc 180
ccggtgaggc cgcatagact gttcccacgg ttgaaagtgg ccgatccgtt atccgctcat 240
gtacttcgag aagcctagta tcgctctgga atcttcgacg cgttgcgctc agcactcaac 300
cccggagtgt agcttgggcc gatgagtctg gacagtcccc actggcgaca gtggtccagg 360
ctgcgctggc ggcccacctg tgcccaaag ccacgggacg ctagttgtga acagggtgtg 420
aagagcctat tgagctacat gagagtcctc cggccctga atgcggctaa tcctaaccat 480
ggagcaggca gctgcaaccc agcagccagc ctgtcgtaac gcgcaagtcc gtggcggaac 540
cgactacttt gggtgtccgt gtttcctttt attcttgaat ggctgcttat ggtgacaatc 600
atagattgtt atcataaagc gagttggatt ggccatccag tgtgaatcag attaattact 660
cccttgtttg ttggatccac tcccgaaacg ttttactcct taacttattg aaattgtttg 720
aagacaggat ttcagtgtca ca ATG
```

Hepatitis C virus IRES-containing mRNA 5'UTR (SEQ ID NO:3):

```
ggtcatcttg gtagccacta taggtgggtc ttaagggttg gtcaaggtcc ctctggcgct  60
tgtggcgaga aagcgcacgg tccacaggtg ttggccctac cggtgtgaat aagggcccga 120
cgtcaggctc gtcgttaaac cgagcccatt acccacctgg gcaaacaacg cccacgtacg 180
gtccacgtcg ccctacaatg tctctcttga ccaataggct ttgccggcga gttgacaagg 240
accagtgggg gctgggcggc gggggaagga cctccgtcgc tgcccttccc ggtggggtgg 300
gaaatgcatg gggccaccca gctccgcggc ggcctgcagc cggggtagcc caananccttt 360
cgggtgaggg cgggtggcat ttttctttcc tataccgatc ATG
```

Insect RNA virus (Plautia stali intestine virus, PSIV) IRES (SEQ ID NO:4):

```
acccucgugc ucgcucaaac auuaaguggu guugugcgaa aagaaucuca cuu CAA      56
```

FIG. 3

Homo sapiens apoptotic protease activating factor 1 (Apaf-1) IRES-containing mRNA 5'UTR (SEQ ID NO:5):

```
     aagaagaggt agcgagtgga cgtgactgct ctatcccggg caaaagggat agaaccagag  60
     gtggggagtc tgggcagtcg gcgacccgcg aagacttgag gtgccgcagc ggcatccgga 120
     gtagcgccgg gctccctccg gggtgcagcc gccgtcgggg aagggcgcc acaggccggg 180
     aagacctcct cccttttgtgt ccagtagtgg ggtccaccgg agggcggcc gtgggccggg 240
     cctcaccgcg gcgctccggg actgtggggt caggctgcgt tgggtggacg cccacctcgc 300
     caaccttcgg aggtccctgg gggtcttcgt gcgcccgg gctgcagaga tccaggggag 360
     gcgcctgtga ggcccggacc tgccccgggg cgaagggtat gtggcgagac agagccctgc 420
     acccctaatt cccggtggaa aactcctgtt gccgtttccc tccaccggcc tggagtctcc 480
     cagtcttgtc ccggcagtgc cgccctcccc actaagacct aggcgcaaag gcttggctca 540
     tggttgacag ctcagagaga gaaagatctg agggaag ATG
```

Human c-myc IRES-containing mRNA 5'UTR (SEQ ID NO:6):

```
     ctgctcgcgg ccgccaccgc cgggcccgg ccgtccctgg ctcccctcct gcctcgagaa  60
     gggcagggct tctcagaggc ttggcgggaa aaagaacgg agggagggat cgcgctgagt 120
     ataaaagccg gttttcgggg ctttatctaa ctcgctgtag taattccagc gagaggcaga 180
     gggagcgagc gggcggccgg ctagggtgga agagccgggc gagcagagct gcgctgcggg 240
     cgtcctggga agggagatcc ggagcgaata gggggcttcg cctctggccc agccctcccg 300
     cttgatcccc caggccagcg gtccgcaacc cttgccgcat ccacgaaact ttgcccatag 360
     cagcgggcgg gcactttgca ctggaactta caacacccga gcaaggacgc gactctcccg 420
     acgcggggag gctattctgc ccatttgggg acacttcccc gccgctgcca ggacccgctt 480
     ctctgaaagg ctctccttgc agctgcttag acgctggatt ttttttcgggt agtggaaaac 540
     cagcagcctc ccgcgacgat gcccctcaac gttagcttca ccaacaggaa ctatgacctc 600
     gactacgact cggtgcagcc gtatttctac tgcgacgagg aggagaactt ctaccagcag 660
     cagcagcaga gcgagctgca gccccggcg cccagcgagg atatctgaa gaaattcgag 720
     ctgctgccca ccccgcccct gtcccctagc cgccgctccg ggctctgctc gccctcctac 780
     gttgcggtca caccettctc ccttcgggga gacaacgacg gcggtggcgg gagcttctcc 940
     acggccgacc agctggag ATG
```

Human BiP IRES-containing 5'UTR 5'UTR (SEQ ID NO:7):

```
     aggtcgacgc cggccaagac agcacagaca gattgaccta ttgggggtgtt tcgcgagtgt  60
     gagagggaag cgccgcggcc tgtatttcta gacctgccct tcgcctggtt cgtggcgcct 120
     tgtgaccccg ggcccctgcc gcctgcaagt cggaaattgc gctgtgctcc tgtgctacgg 180
     cctgtggctg gactgcctgc tgctgcccaa ctggctggca ag ATG
```

Homo sapiens eIF4GII IRES-containing mRNA 5'UTR (SEQ ID NO:8):

```
     caatcccaca gagtattgat gaggaaactg aagtttggag cgatcacatc attttcccaa  60
     ggtaacacaa gtggcaagac agccgggaac ccctacccca tcccctttatt cagcacatga 120
     aataaacaag gggcatccaa atcttgcggc aacgccccg ggacatgcat cgtcccctgg 180
     actctctcaa acccctttatc cctctggaca gaatgcaggt ccaaccacgc tggtataccc 240
     tcaaacccct cagaca ATG
```

Rattus norvegicus fibroblast growth factor 2 IRES-containing mRNA 5'UTR (SEQ ID NO:9):

```
                gcggggc gcgcggggcc ggggtgcagg cggggacgcg ggggtgacgc  48
     gggcccggc cgctgtagca cacaggggct cggtctctcg gcttcaggcg gagtccggct 108
     gcactaggct gggagcgcgg cgggacgcga accgggaggc tggcagcccg cgggcgagcc 168
     gcgctggggg gccgaggccg gggtcggggc cggggagccc cgagagctgc cgcagcgggg 228
     tcccggggcc gcggagggc c ATG
```

*FIG. 3 (CONT'D.)*

Homo sapiens vascular endothelial growth factor C IRES (SEQ ID NO:10):
```
                            ggcactggc tgggagggcg ccctgcaaag ttgggaacgc   960
ggagcccgg acccgctccc gccgcctccg gctcgcccag gggggtcgc cgggaggagc  1020
ccgggggaga gggaccagga ggggcccgcg gcctcgcagg ggcgcccgcg cccccacccc  1080
tgcccccgcc agcggaccgg tcccccaccc ccggtccttc cacc ATG
```

Rattus norvegicus X-linked inhibitor of apoptosis (riap3) IRES (SEQ ID NO:11):
```
gtcaggctct ggcttggagc tggggaggcg gggtggggggg gtggggggggg tcgggctgca    60
taatgaggac tggggggtttt ttggatgccc ccttccggct ccgcgagacg gcggaccttg   120
gcggtccccc gagcgagcgc gacgctaatc gagggctgct cggctcgaga ggccggggcc   180
cgccgcccag cagagttgtg ttttcctga tcgggctcg ggccgcccct cctccgggac    240
cctccctcg ggaaccgtcg cccgcggcgg ttagttagga ctggattgct tggcgcgaaa    300
aggtggacaa gtcgtatttt caagagaag ATG
```

Gtx homeodomain protein 5'UTR IRES (SEQ ID NO:12):
```
cccgagccgg cgggugcggg cgguggcagc ggggcccgga ugggcgcccg g             51
```

FIG. 3 (CONT'D.)

▓ Grey bar designates Gtx IRES GC-rich module (CCGGCGGGU)

■ Black bar designates different 9-nt sequences taken from the mouse beta-globin 5'UTR, which is unable functioning as an IRES ▯ 25 nt of the mouse beta-globin 5'UTR sequence immediately upstream of the iniation codon and Gallie, 1999; Tacke et al., 1990; Thomas et al., 1991).

SEQUENCE LISTING

<160> NUMBER OF SEQ ID NOS: 64

<210> SEQ ID NO 1
<211> LENGTH: 884
<212> TYPE: DNA
<213> ORGANISM: Encephalomyocarditis virus

<400> SEQUENCE: 1

```
ttgaaagccg ggggtgggag atccggattg ccagtctact cgatatcgca ggctgggtcc      60
gtgactaccc actcctactt tcaacgtgaa ggctacgata gtgccagggc gggtactgcc     120
gtaagtgcca ccccaaccaa caaaacaaaa accccccccc cccccccccc cccccccccc     180
cccccccccc cccccccccc cccccccccc cccccccccc cccccccccc cccccccccc     240
cccccccccc cccccccccc ccccccccca acgttactgg ccgaagccgc ttggaataag     300
gccggtgtgc gtttgtctat atgttatttc taccacatca ccgtcttttg gtggtgtgag     360
ggcccggaac ctggccctgt cttcttgacg agcattccta ggggtctttc ccctctcgcc     420
aaaggaatgt aaggtctgtt gaatgtcgtg aaggaagcag ttcctctgga agcttcttga     480
agacaagcaa cgtctgtagc gacccttttgc aggcagcgga atccccacc tggtaacagg     540
tgcctctgcg gccaaaagcc acgtgtataa gatacacctg caaaggcggc acaaccccag     600
tgccacgttg tgagttggat agttgtggaa agagtcaaat ggctcacctc aagcgtattc     660
aacaaggggc tgaaggatgc ccagaaggta ccccattgta tgggatctga tctgggggcct     720
cggtgcacgt gctctacacg tgttgagtcg aggttaaaaa acgtctaggc cccccgaacc     780
acggggacgt ggttttcctt tgaaaaccac gattgtaaga tggctacaac tatggaacaa     840
gagatttgtg cgcattccct cacgtttaaa ggatgcccga aatg                       884
```

<210> SEQ ID NO 2
<211> LENGTH: 745
<212> TYPE: DNA
<213> ORGANISM: Polianthes geminiflora

<400> SEQUENCE: 2

```
ttaaaacagc tctggggttg ttcccacccc agaggcccac gtggcggcta gtacactggt      60
atcacggtac ctttgtacgc ctgttttata ctccctcccc cgcaacttag aagcatacaa     120
ttcaagctca ataggagggg gtgcaagcca gcgcctccgt gggcaagcac tactgtttcc     180
ccggtgaggc cgcatagact gttcccacgg ttgaaagtgg ccgatccgtt atccgctcat     240
gtacttcgag aagcctagta tcgctctgga atcttcgacg cgttgcgctc agcactcaac     300
cccggagtgt agcttgggcc gatgagtctg gacagtcccc actggcgaca gtggtccagg     360
ctgcgctggc ggcccacctg tgcccaaag ccacgggacg ctagttgtga acagggtgtg     420
aagagcctat tgagctacat gagagtcctc cggcccctga atgcggctaa tcctaaccat     480
ggagcaggca gctgcaaccc agcagccagc ctgtcgtaac gcgcaagtcc gtggcggaac     540
cgactacttt gggtgtccgt gtttccttttt attcttgaat ggctgcttat ggtgacaatc     600
atagattgtt atcataaagc gagttggatt ggccatccag tgtgaatcag attaattact     660
cccttgtttg ttggatccac tcccgaaacg ttttactcct taacttattg aaattgtttg     720
aagacaggat ttcagtgtca caatg                                            745
```

<210> SEQ ID NO 3
<211> LENGTH: 403
<212> TYPE: DNA

```
<213> ORGANISM: Hepatitis C virus
<220> FEATURE:
<221> NAME/KEY: misc_feature
<222> LOCATION: (354)..(354)
<223> OTHER INFORMATION: unknown
<220> FEATURE:
<221> NAME/KEY: misc_feature
<222> LOCATION: (356)..(356)
<223> OTHER INFORMATION: unknown

<400> SEQUENCE: 3
ggtcatcttg gtagccacta taggtgggtc ttaagggttg gtcaaggtcc ctctggcgct      60
tgtggcgaga aagcgcacgg tccacaggtg ttggccctac cggtgtgaat aagggcccga     120
cgtcaggctc gtcgttaaac cgagcccatt acccacctgg gcaaacaacg cccacgtacg     180
gtccacgtcg ccctacaatg tctctcttga ccaataggct ttgccggcga gttgacaagg     240
accagtgggg gctgggcggc gggggaagga cctccgtcgc tgcccttccc ggtggggtgg     300
gaaatgcatg gggccaccca gctccgcggc ggcctgcagc cggggtagcc caanancctt     360
cgggtgaggg cgggtggcat ttttctttcc tataccgatc atg                       403

<210> SEQ ID NO 4
<211> LENGTH: 56
<212> TYPE: RNA
<213> ORGANISM: Plautia stali intestine virus

<400> SEQUENCE: 4
acccucgugc ucgcucaaac auuaaguggu guugugcgaa aagaaucuca cuucaa          56

<210> SEQ ID NO 5
<211> LENGTH: 580
<212> TYPE: DNA
<213> ORGANISM: Homo sapiens

<400> SEQUENCE: 5
aagaagaggt agcgagtgga cgtgactgct ctatcccggg caaaagggat agaaccagag      60
gtggggagtc tgggcagtcg gcgacccgcg aagacttgag gtgccgcagc ggcatccgga     120
gtagcgccgg gctccctccg gggtgcagcc gccgtcgggg gaagggcgcc acaggccggg     180
aagacctcct cccttttgtgt ccagtagtgg ggtccaccgg agggcggccc gtgggccggg    240
cctcaccgcg gcgctccggg actgtggggt caggctgcgt tgggtggacg cccacctcgc     300
caaccttcgg aggtccctgg gggtcttcgt gcgccccggg gctgcagaga tccaggggag     360
gcgcctgtga ggcccggacc tgccccgggg cgaagggtat gtggcgagac agagccctgc     420 accctaatt cccggtggaa aactcctgtt gccgtttccc tccaccggcc tggagtctcc      480
cagtcttgtc ccggcagtgc cgccctcccc actaagacct aggcgcaaag gcttggctca    540
tggttgacag ctcagagaga gaaagatctg agggaagatg                           580

<210> SEQ ID NO 6
<211> LENGTH: 861
<212> TYPE: DNA
<213> ORGANISM: Homo sapiens

<400> SEQUENCE: 6
ctgctcgcgg ccgccaccgc cggggcccgg ccgtccctgg ctcccctcct gcctcgagaa      60
gggcagggct tctcagaggc ttggcgggaa aaaagaacgg agggagggat cgcgctgagt     120
ataaaagccg gttttcgggg ctttatctaa ctcgctgtag taattccagc gagaggcaga     180
gggagcgagc gggcggccgg ctagggtgga agagccgggc gagcagagct gcgctgcggg     240
```

| | |
|---|---|
| cgtcctggga agggagatcc ggagcgaata gggggcttcg cctctggccc agccctcccg | 300 |
| cttgatcccc caggccagcg gtccgcaacc cttgccgcat ccacgaaact ttgcccatag | 360 |
| cagcgggcgg gcactttgca ctggaactta caacacccga gcaaggacgc gactctcccg | 420 |
| acgcggggag gctattctgc ccatttgggg acacttcccc gccgctgcca ggacccgctt | 480 |
| ctctgaaagg ctctccttgc agctgcttag acgctggatt tttttcgggt agtggaaaac | 540 |
| cagcagcctc ccgcgacgat gcccctcaac gttagcttca ccaacaggaa ctatgacctc | 600 |
| gactacgact cggtgcagcc gtatttctac tgcgacgagg aggagaactt ctaccagcag | 660 |
| cagcagcaga gcgagctgca gccccggcg cccagcgagg atatctggaa gaaattcgag | 720 |
| ctgctgccca ccccgcccct gtcccctagc cgccgctccg ggctctgctc gccctcctac | 780 |
| gttgcggtca caccctttctc ccttcgggga gacaacgacg gcggtggcgg gagcttctcc | 840 |
| acggccgacc agctggagat g | 861 |

<210> SEQ ID NO 7
<211> LENGTH: 225
<212> TYPE: DNA
<213> ORGANISM: Homo sapiens

<400> SEQUENCE: 7

| | |
|---|---|
| aggtcgacgc cggccaagac agcacagaca gattgaccta ttggggtgtt tcgcgagtgt | 60 |
| gagagggaag cgccgcggcc tgtatttcta gacctgccct tcgcctggtt cgtggcgcct | 120 |
| tgtgaccccg ggcccctgcc gcctgcaagt cggaaattgc gctgtgctcc tgtgctacgg | 180 |
| cctgtggctg gactgcctgc tgctgcccaa ctggctggca agatg | 225 |

<210> SEQ ID NO 8
<211> LENGTH: 259
<212> TYPE: DNA
<213> ORGANISM: Homo sapiens

<400> SEQUENCE: 8

| | |
|---|---|
| caatcccaca gagtattgat gaggaaactg aagtttggag cgatcacatc attttcccaa | 60 |
| ggtaacacaa gtggcaagac agccgggaac ccctacccca tccccttatt cagcacatga | 120 |
| aataaacaag gggcatccaa atcttgcggc aacgcccccg ggacatgcat cgtcccctgg | 180 |
| actctctcaa accccttatc cctctggaca gaatgcaggt ccaaccacgc tggtataccc | 240 |
| tcaaacccct cagacaatg | 259 |

<210> SEQ ID NO 9
<211> LENGTH: 252
<212> TYPE: DNA
<213> ORGANISM: Rattus norvegicus

<400> SEQUENCE: 9

| | |
|---|---|
| gcggggcgc gcggggccgg ggtgcaggcg gggacgcggg ggtgacgcgg gcccgggccg | 60 |
| ctgtagcaca caggggctcg gtctctcggc ttcaggcgga gtccggctgc actaggctgg | 120 |
| gagcgcggcg ggacgcgaac cgggaggctg gcagcccgcg ggcgagccgc gctgggggc | 180 |
| cgaggccggg gtcggggccg gggagccccg agagctgccg cagcggggtc ccggggccgc | 240 |
| ggaggggcca tg | 252 |

<210> SEQ ID NO 10
<211> LENGTH: 206
<212> TYPE: DNA
<213> ORGANISM: Homo sapiens -continued

<400> SEQUENCE: 10

```
ggcactggct gggagggcgc cctgcaaagt tgggaacgcg gagccccgga cccgctcccg    60
ccgcctccgg ctcgcccagg gggggtcgcc gggaggagcc cggggagag ggaccaggag    120
gggcccgcgg cctcgcaggg gcgcccgcgc ccccacccct gccccgcca gcggaccggt    180
cccccacccc cggtccttcc accatg                                        206
```

<210> SEQ ID NO 11
<211> LENGTH: 332
<212> TYPE: DNA
<213> ORGANISM: Rattus norvegicus

<400> SEQUENCE: 11

```
gtcaggctct ggcttggagc tggggaggcg gggtggggg gtgggggggg tcgggctgca    60
taatgaggac tgggggtttt ttggatgccc ccttccggct ccgcgagacg gcggaccttg    120
gcggtccccc gagcgagcgc gacgctaatc gagggctgct cggctcgaga ggccggggcc    180
cgccgcccag cagagttgtg tttttcctga tcggggctcg ggccgcccct cctccgggac    240
cctcccctcg ggaaccgtcg cccgcggcgg ttagttagga ctggattgct tggcgcgaaa    300
aggtggacaa gtcgtatttt caagagaaga tg                                332
```

<210> SEQ ID NO 12
<211> LENGTH: 51
<212> TYPE: RNA
<213> ORGANISM: Homo sapiens

<400> SEQUENCE: 12

```
cccgagccgg cgggtgcggg cggtggcagc ggggcccgga ugggcgcccg g             51
```

<210> SEQ ID NO 13
<211> LENGTH: 55
<212> TYPE: DNA
<213> ORGANISM: Artificial Sequence
<220> FEATURE:
<223> OTHER INFORMATION: oligo for constructing artificial IRES

<400> SEQUENCE: 13

```
cgcgcaagct taaaagaagg aaaagaaagg aaaagaagga aaaagaaggc tgcag         55
```

<210> SEQ ID NO 14
<211> LENGTH: 60
<212> TYPE: DNA
<213> ORGANISM: Artificial Sequence
<220> FEATURE:
<223> OTHER INFORMATION: oligo for constructing artificial IRES

<400> SEQUENCE: 14

```
cccgcctgca gccttctttt tccttctttt ccttcttttt ccttctttta agcttgcgcg    60
```

<210> SEQ ID NO 15
<211> LENGTH: 58
<212> TYPE: DNA
<213> ORGANISM: Artificial Sequence
<220> FEATURE:
<223> OTHER INFORMATION: oligo for constructing artificial IRES

<400> SEQUENCE: 15

```
ggcggctgca gaaaagaagg aaaagaagg aaaagaagga aaaagaagga attcgggc       58
```

<210> SEQ ID NO 16
<211> LENGTH: 58
<212> TYPE: DNA

<213> ORGANISM: Artificial Sequence
<220> FEATURE:
<223> OTHER INFORMATION: oligo for constructing artificial IRES

<400> SEQUENCE: 16
gcccgaattc cttcttttc cttctttcc ttcttttcc ttcttttctg cagccgcc    58

<210> SEQ ID NO 17
<211> LENGTH: 102
<212> TYPE: DNA
<213> ORGANISM: Artificial Sequence
<220> FEATURE:
<223> OTHER INFORMATION: Artificial IRES

<400> SEQUENCE: 17
cgcgcaagct taaaagaagg aaaagaagg aaaagaagga aaagaaggc tgcagaaaag    60 aaggaaaaag aaggaaaaga aggaaaaga aggaattcgg gc    102

<210> SEQ ID NO 18
<211> LENGTH: 102
<212> TYPE: DNA
<213> ORGANISM: Artificial Sequence
<220> FEATURE:
<223> OTHER INFORMATION: Artificial IRES

<400> SEQUENCE: 18
gcgcgttcga attttcttcc tttttcttcc ttttcttcct ttttcttccg acgtcttttc    60
ttcctttttc ttcctttttct tcctttttct tccttaagcc cg    102

<210> SEQ ID NO 19
<211> LENGTH: 48
<212> TYPE: DNA
<213> ORGANISM: Artificial Sequence
<220> FEATURE:
<223> OTHER INFORMATION: oligo for constructing artificial IRES

<400> SEQUENCE: 19
ccgcgcaagc ttagaaagaa agaaagaaag aaagaaagaa actgcagc    48

<210> SEQ ID NO 20
<211> LENGTH: 54
<212> TYPE: DNA
<213> ORGANISM: Artificial Sequence
<220> FEATURE:
<223> OTHER INFORMATION: oligo for constructing artificial IRES

<400> SEQUENCE: 20
cgcggcgctg cagtttcttt ctttctttct ttctttcttt ctaagcttgc gcgg    54

<210> SEQ ID NO 21
<211> LENGTH: 56
<212> TYPE: DNA
<213> ORGANISM: Artificial Sequence
<220> FEATURE:
<223> OTHER INFORMATION: oligo for constructing artificial IRES

<400> SEQUENCE: 21
gccgcgcctg cagaaagaaa gaaagaaaga agaaagaaa gaaagaattc cgccgc    56

<210> SEQ ID NO 22
<211> LENGTH: 56
<212> TYPE: DNA
<213> ORGANISM: Artificial Sequence
<220> FEATURE:
<223> OTHER INFORMATION: oligo for constructing artificial IRES -continued

```
<400> SEQUENCE: 22
gcggcggaat ctttctttc tttctttctt tctttcttc tttctgcagg cgcggc        56

<210> SEQ ID NO 23
<211> LENGTH: 90
<212> TYPE: DNA
<213> ORGANISM: Artificial Sequence
<220> FEATURE:
<223> OTHER INFORMATION: Artificial IRES

<400> SEQUENCE: 23
ccgcgcaagc ttagaaagaa agaaagaaag aaagaaagaa actgcagaaa gaaagaaaga   60
aagaaagaaa gaaagaaaga attccgccgc                                   90

<210> SEQ ID NO 24
<211> LENGTH: 90
<212> TYPE: DNA
<213> ORGANISM: Artificial Sequence
<220> FEATURE:
<223> OTHER INFORMATION: Artificial IRES

<400> SEQUENCE: 24
ggcgcgttcg aatctttctt tctttctttc tttctttctt tgacgtcttt ctttctttct   60
ttctttcttt ctttctttct taaggcggcg                                   90

<210> SEQ ID NO 25
<211> LENGTH: 54
<212> TYPE: DNA
<213> ORGANISM: Artificial Sequence
<220> FEATURE:
<223> OTHER INFORMATION: Oligo for constructing artificial IRES

<400> SEQUENCE: 25
ccgcgcaagc tttgtttgtt tgtttgtttg tttgtttgtt tctgcagcgc cgcg         54

<210> SEQ ID NO 26
<211> LENGTH: 54
<212> TYPE: DNA
<213> ORGANISM: Artificial Sequence
<220> FEATURE:
<223> OTHER INFORMATION: Oligo for constructing artificial IRES

<400> SEQUENCE: 26
cgcggcgctg cagaaacaaa caaacaaaca aacaaacaaa caaagcttgc gcgg         54

<210> SEQ ID NO 27
<211> LENGTH: 56
<212> TYPE: DNA
<213> ORGANISM: Artificial Sequence
<220> FEATURE:
<223> OTHER INFORMATION: Oligo for constructing artificial IRES

<400> SEQUENCE: 27
ccgcgcctgc agtttgtttg tttgtttgtt tgtttgtttg tttgaattcc gccgcg       56

<210> SEQ ID NO 28
<211> LENGTH: 56
<212> TYPE: DNA
<213> ORGANISM: Artificial Sequence
<220> FEATURE:
<223> OTHER INFORMATION: Oligo for constructing artificial IRES

<400> SEQUENCE: 28
cgcggcggaa ttcaaacaaa caaacaaaca aacaaacaaa caaactgcag gcgcgg       56
```

```
<210> SEQ ID NO 29
<211> LENGTH: 91
<212> TYPE: DNA
<213> ORGANISM: Artificial Sequence
<220> FEATURE:
<223> OTHER INFORMATION: Artificial IRES

<400> SEQUENCE: 29
ccgcgcaagc tttgtttgtt tgtttgtttg tttgtttgtt tctgcagttt gtttgtttgt      60
ttgtttgttt gtttgtttga attccgccgc g                                    91

<210> SEQ ID NO 30
<211> LENGTH: 91
<212> TYPE: DNA
<213> ORGANISM: Artificial Sequence
<220> FEATURE:
<223> OTHER INFORMATION: Artificial IRES

<400> SEQUENCE: 30
ggcgcgttcg aaacaaacaa acaaacaaac aaacaaacaa agacgtcaaa caaacaaaca      60
aacaaacaaa caaacaaact taaggcggcg c                                    91

<210> SEQ ID NO 31
<211> LENGTH: 16
<212> TYPE: RNA
<213> ORGANISM: Artificial Sequence
<220> FEATURE:
<223> OTHER INFORMATION: Emp x 4 element

<400> SEQUENCE: 31
uuugcuuuuu guagua                                                     16

<210> SEQ ID NO 32
<211> LENGTH: 60
<212> TYPE: DNA
<213> ORGANISM: Artificial Sequence
<220> FEATURE:
<223> OTHER INFORMATION: Oligo for constructing artificial IRES

<400> SEQUENCE: 32
gcccgaattc tactacaaaa agcaaacgta ctacaaaaag caaactgcag ccgccgcggg      60

<210> SEQ ID NO 33
<211> LENGTH: 54
<212> TYPE: DNA
<213> ORGANISM: Artificial Sequence
<220> FEATURE:
<223> OTHER INFORMATION: Oligo for constructing artificial IRES

<400> SEQUENCE: 33
cccgcctgca gtactacaaa aagcaaacgt actacaaaaa cgaaagcttg cgcg            54

<210> SEQ ID NO 34
<211> LENGTH: 55
<212> TYPE: DNA
<213> ORGANISM: Artificial Sequence
<220> FEATURE:
<223> OTHER INFORMATION: Oligo for constructing artificial IRES

<400> SEQUENCE: 34
ggcggctgca gtttgctttt tgtagtacgt ttgcttttg tagtagaatt cgggc            55

<210> SEQ ID NO 35
<211> LENGTH: 55
<212> TYPE: DNA
```

<213> ORGANISM: Artificial Sequence
<220> FEATURE:
<223> OTHER INFORMATION: Oligo for constructing artificial IRES

<400> SEQUENCE: 35
gcccgaattc tactacaaaa agcaaacgta ctacaaaaag caaactgcag ccgcc        55

<210> SEQ ID NO 36
<211> LENGTH: 99
<212> TYPE: DNA
<213> ORGANISM: Artificial Sequence
<220> FEATURE:
<223> OTHER INFORMATION: Artificial IRES

<400> SEQUENCE: 36
gcccgaattc tactacaaaa agcaaacgta ctacaaaaag caaactgcag ccgcctttgc    60
tttttgtagt acgtttgctt tttgtagtag aattcgggc                          99

<210> SEQ ID NO 37
<211> LENGTH: 99
<212> TYPE: DNA
<213> ORGANISM: Artificial Sequence
<220> FEATURE:
<223> OTHER INFORMATION: Artificial IRES

<400> SEQUENCE: 37
cgggcttaag atgatgtttt tcgtttgcat gatgtttttc gtttgacgtc ggcggaaacg    60
aaaaacatca tgcaaacgaa aaacatcatc ttaagcccg                          99

<210> SEQ ID NO 38
<211> LENGTH: 88
<212> TYPE: DNA
<213> ORGANISM: Artificial Sequence
<220> FEATURE:
<223> OTHER INFORMATION: Oligo for constructing artificial IRES

<400> SEQUENCE: 38
cgcggaagct tcgcgggcgt tgttcgcgg gcgtttgttc gcgggcgttt gttcgcgggc    60
gtttgttctt tgtttgagaa ttccgcgc                                      88

<210> SEQ ID NO 39
<211> LENGTH: 89
<212> TYPE: DNA
<213> ORGANISM: Artificial Sequence
<220> FEATURE:
<223> OTHER INFORMATION: Oligo for constructing artificial IRES

<400> SEQUENCE: 39
gcgcggaatt ccaaacaaag aacaaacgcc cgcgaacaac gcccgcgaac aaacgcccgc    60
gaacaaacgc ccgcgaaaaa gcttccgcg                                     89

<210> SEQ ID NO 40
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 40
cgcggaagct taaaaaaaaa aaaaaaaaaa aaaaaaaaaa aaaaaaaaaa aaaaaaaaa    60 aaaaaaaaaa aaccatggcg cgc                                           83

<210> SEQ ID NO 41

<211> LENGTH: 84
<212> TYPE: DNA
<213> ORGANISM: Artificial Sequence
<220> FEATURE:
<223> OTHER INFORMATION: Oligo for constructing artificial IRES

<400> SEQUENCE: 41
gcgcgccatg gtttttttt tttttttttt tttttttttt tttttttttt    60
tttttttttt tttaagcttc cgcg    84

<210> SEQ ID NO 42
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 42
cgcggaagct tgggggggg gggggggggg gggggggggg gggggggggg    60
gggggggggg ggccatggcg cgc    83

<210> SEQ ID NO 43
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 43
gcgcgccatg gcccccccc cccccccccc cccccccccc cccccccccc    60
cccccccccc ccaagcttcc gcg    83

<210> SEQ ID NO 44
<211> LENGTH: 86
<212> TYPE: DNA
<213> ORGANISM: Artificial Sequence
<220> FEATURE:
<223> OTHER INFORMATION: Oligo for constructing artificial IRES

<400> SEQUENCE: 44
gcgcgaagct taaacaaaca aacaaacaaa caaacaaaca aacaaacaaa caaacaaaca    60
aacaaacaaa caaaccatgg cgcggc    86

<210> SEQ ID NO 45
<211> LENGTH: 83
<212> TYPE: RNA
<213> ORGANISM: Artificial Sequence
<220> FEATURE:
<223> OTHER INFORMATION: Oligo for constructing artificial IRES

<400> SEQUENCE: 45
gccgcgccau ggguuuguuu guuuguuugu uguuuguuu guuuguuugu uguuuguuu    60 guuuguuugu uuaagcuucg cgc    83

<210> SEQ ID NO 46
<211> LENGTH: 87
<212> TYPE: DNA
<213> ORGANISM: Artificial Sequence
<220> FEATURE:
<223> OTHER INFORMATION: Oligo for constructing artificial IRES

<400> SEQUENCE: 46
gcgcgaagct taaataaata aataaataaa taaataaata aataaataaa taaataaata    60
aataaataaa taaatccatg gcgcggc 87

<210> SEQ ID NO 47
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 47
gccgcgccat ggatttattt atttatttat ttatttattt atttatttat ttatttattt 60
atttatttat ttaagcttcg cgc 83

<210> SEQ ID NO 48
<211> LENGTH: 87
<212> TYPE: DNA
<213> ORGANISM: Artificial Sequence
<220> FEATURE:
<223> OTHER INFORMATION: Oligo for constructing artificial IRES

<400> SEQUENCE: 48
gcgcgaagct tgaacgaacg aacgaacgaa cgaacgaacg aacgaacgaa cgaacgaacg 60
aacgaacgaa cgaacccatg gcgcggc 87

<210> SEQ ID NO 49
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 49
gccgcgccat gggttcgttc gttcgttcgt tcgttcgttc gttcgttcgt tcgttcgttc 60
gttcgttcgt tcaagcttcg cgc 83

<210> SEQ ID NO 50
<211> LENGTH: 87
<212> TYPE: DNA
<213> ORGANISM: Artificial Sequence
<220> FEATURE:
<223> OTHER INFORMATION: Oligo for constructing artificial IRES

<400> SEQUENCE: 50
gcgcgaagct tgaatgaatg aatgaatgaa tgaatgaatg aatgaatgaa tgaatgaatg 60
aatgaatgaa tgaatccatg gcgcggc 87

<210> SEQ ID NO 51
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 51
gccgcgccat ggattcattc attcattcat tcattcattc attcattcat tcattcattc 60
attcattcat tcaagcttcg cgc 83

<210> SEQ ID NO 52
<211> LENGTH: 83
<212> TYPE: DNA
<213> ORGANISM: Artificial Sequence
<220> FEATURE:
<223> OTHER INFORMATION: Oligo for constructing artificial IRES

```
<400> SEQUENCE: 52
gcgcgaagct taaaacaaaa caaaacaaaa caaaacaaaa caaaacaaaa caaaacaaaa      60
caaaacaaaa cccatggcgc ggc                                             83

<210> SEQ ID NO 53
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 53
gccgcgccat gggttttgtt ttgttttgtt ttgttttgtt ttgttttgtt ttgttttgtt      60
ttgttttgtt ttaagcttcg cgc                                             83

<210> SEQ ID NO 54
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 54
gcgcgaagct taaaataaaa taaaataaaa taaaataaaa taaaataaaa taaaataaaa      60
taaaataaaa tccatggcgc ggc                                             83

<210> SEQ ID NO 55
<211> LENGTH: 83
<212> TYPE: DNA
<213> ORGANISM: Artificial Sequence
<220> FEATURE:
<223> OTHER INFORMATION: Oligo for constructing artificial IRES

<400> SEQUENCE: 55
gccgcgccat ggcttttctt ttcttttctt ttcttttctt ttcttttctt ttcttttctt      60
ttcttttctt ttaagcttcg cgc                                             83

<210> SEQ ID NO 56
<211> LENGTH: 87
<212> TYPE: DNA
<213> ORGANISM: Artificial Sequence
<220> FEATURE:
<223> OTHER INFORMATION: Oligo for constructing artificial IRES

<400> SEQUENCE: 56
gcgcgaagct taaggaagga aggaaggaag gaaggaagga aggaaggaag gaaggaagga      60
aggaaggaag gaaggccatg gcgcggc                                         87

<210> SEQ ID NO 57
<211> LENGTH: 87
<212> TYPE: DNA
<213> ORGANISM: Artificial Sequence
<220> FEATURE:
<223> OTHER INFORMATION: Oligo for constructing artificial IRES

<400> SEQUENCE: 57
gccgcgccat ggccttcctt ccttccttcc ttccttcctt ccttccttcc ttccttcctt      60
ccttccttcc ttccttaagc ttcgcgc                                         87

<210> SEQ ID NO 58
<211> LENGTH: 87
<212> TYPE: DNA
```

<213> ORGANISM: Artificial Sequence
<220> FEATURE:
<223> OTHER INFORMATION: Oligo for constructing artificial IRES

<400> SEQUENCE: 58
gcgcgaagct tagggaggga gggagggagg gagggaggga gggagggagg gagggaggga    60
gggagggagg gagggccatg gcgcggc                                        87

<210> SEQ ID NO 59
<211> LENGTH: 87
<212> TYPE: DNA
<213> ORGANISM: Artificial Sequence
<220> FEATURE:
<223> OTHER INFORMATION: Oligo for constructing artificial IRES

<400> SEQUENCE: 59
gccgcgccat ggccctccct ccctccctcc ctccctccct ccctccctcc ctccctccct    60
ccctccctcc ctccctaagc ttcgcgc                                        87

<210> SEQ ID NO 60
<211> LENGTH: 66
<212> TYPE: DNA
<213> ORGANISM: Artificial Sequence
<220> FEATURE:
<223> OTHER INFORMATION: sequence designed for forming a hairpin

<400> SEQUENCE: 60
ggtaccgggc ccccccctcga ggtcgacggt atcgataccg tcgacctcga ggggggggccc    60 ggtacc                                                               66

<210> SEQ ID NO 61
<211> LENGTH: 31
<212> TYPE: DNA
<213> ORGANISM: Artificial Sequence
<220> FEATURE:
<223> OTHER INFORMATION: PCR primer

<400> SEQUENCE: 61
ccggatcctt atggtgagca agggcgagga g                                   31

<210> SEQ ID NO 62
<211> LENGTH: 29
<212> TYPE: DNA
<213> ORGANISM: Artificial Sequence
<220> FEATURE:
<223> OTHER INFORMATION: PCR primer

<400> SEQUENCE: 62
cgcaagctta cttgtacagc tcgtccatg                                      29

<210> SEQ ID NO 63
<211> LENGTH: 64
<212> TYPE: DNA
<213> ORGANISM: Artificial
<220> FEATURE:
<223> OTHER INFORMATION: Artificial IRES element

<400> SEQUENCE: 63
gaaagaaaga agaaagaaa gaaagaaaga agaaagaaa gaaagaaaga agaaagaaa      60 gaaa                                                                 64

<210> SEQ ID NO 64
<211> LENGTH: 64
<212> TYPE: RNA

-continued

```
<213> ORGANISM: Artificial
<220> FEATURE:
<223> OTHER INFORMATION: Artificial IRES

<400> SEQUENCE: 64
guuuguuugu uuguuuguuu guuuguuugu uuguuuguuu guuuguuugu uuguuuguuu      60
guuu                                                                  64
```

CREATION OF ARTIFICIAL INTERNAL RIBOSOME ENTRY SITE (IRES) ELEMENTS

CROSS-REFERENCE TO RELATED APPLICATIONS

The present application is a 35 U.S.C. §371 National Phase Application of International Application Serial No. PCT/EP02/09843, filed Sep. 3, 2002 and published in English as PCT Publication No. WO 03/020927 on Mar. 13, 2003, which claims priority to German Patent Application Serial No. DE 101 43 237.2, filed Sep. 4, 2001, the disclosures of each of which are incorporated herein by reference in their entireties.

FIELD OF THE INVENTION

The present invention is directed to a method of creating artificial internal ribosome entry site (IRES) elements capable of causing cap-independent translation of a nucleotide sequence of interest in eukaryotic cells or organisms. Further, a process of expressing a nucleotide sequence of interest in eukaryotic cells under translational control of an artificial IRES element according to the invention is provided. The invention further relates to a vector and an expression cassette comprising such an IRES element and to eukaryotic cells transformed or transfected with such a vector or expression cassette.

BACKGROUND OF THE INVENTION

There is a growing interest in using internal ribosome entry site (IRES) elements for expressing foreign genes in eukaryotic cells. Although the number of nucleotide sequences that are capable to provide cap-independent translation increases constantly, identification of new IRESes has been occasional or accidental without distinct methodology of predicting IRES elements.

In most cases, the regulation of translation in eukaryotic cells occurs at the stage of initiation by a scanning mechanism. This involves binding of eukaryotic initiation factor 4F (eIF4F), a complex of proteins which includes eIF4E (the cap binding protein), eIF4G (a large protein which acts as a scaffold for the proteins in the complex and has binding sites for eIF4E, eIF4a, eIF3, and a poly(A) binding protein), and eIF4A (RNA helicase) to the m7GpppN cap structure, recruitment of a 40 S ribosomal subunit, and scanning to the first AUG codon in the correct context (Pain, V. M., 1996, Eur. J. Biochem. 236, 747-771).

Translation initiation can also occur by a mechanism that does not require the cap structure. In this case, the ribosome enters the mRNA at a region termed an internal ribosome entry site (IRES) that is up to 1,000 bp long. IRESes were originally identified in picornaviral RNAs, and during picornaviral infection, there is often a switch of translation from host encoded cellular mRNAs to viral transcripts (Jackson and Kaminski, 1995, RNA 1, 985-1000).

IRES-containing animal mRNAs can presumably recruit 40 S ribosomes either via their capped 5' ends or their IRES elements, which likely allows translation under conditions when cap-dependent translation is reduced as, for example, during viral infection, at the G2/M phase of cell cycle, apoptosis or stress conditions (Johannes et al., (1999) Proc. Natl. Acad. Sci. USA 96, 13118-13123; Cornelis et al., (2000) Molecular Cell 5, 597-605; Pyronnet et al., (2000) Molecular Cell 5, 607-616; Stein et al., 1998 Mol. and Cell. Biol. 18, 3112-3119; Holcik et al., 2000 Oncogene 19, 4174-4177; Stoneley et al., 2000 Mol. and Cell. Biol. 20, 1162-1169). Up to 3% of animal cellular mRNAs are translated despite that eIF4F-RNA binding is inhibited (Johannes et al., 1999).

In contrast to animal cellular mRNA, there are no published reports concerning IRES-mediated initiation of translation in plant cells in vivo. However, the uncapped 5' leaders of several plant viral genomic RNAs including poty-, como-, and luteoviruses are responsible for cap-independent translation (Carrington and Freed, 1990; Gallie et al., 1995; Niepel and Gallie, 1999; Tacke et al., 1990; Thomas et al., 1991). Tobamoviruses and potexvirus X are the only examples of IRESes located in internal parts of viral genomes (Hefferon et al., 1997 J. Gen. Virol. 78, 3051-3059; Hefferon et al., 2000 Arch. Virol. 145, 945-956; Ivanov et al., (1997) Virology 232, 32-43; Skulachev et al., (1999) Virology 263, 139-154).

Tobacco mosaic tobamovirus (TMV) is a positive-stranded RNA plant virus with a monopartite genome of 6395 nucleotides (nt) in length (Goelet et al., 1982 Proc. Natl. Acad. Sci. USA 79, 5818-5822). The 5' proximal ORFs encoding replicative proteins are expressed directly from the genomic RNA and the level of synthesis of the smaller (126 kDa) protein is approximately 10 times higher than the level of the 183 kDa protein which is produced by occasional readthrough of the stop codon for the 126-kDa ORF (Siegel et al., 1976 Virology 73, 363-371). Although some replication can occur with the larger protein only, both proteins are required for efficient replication (Ishikawa et al., 1986). The remaining TMV gene products, the movement protein (MP) and the coat protein (CP), are expressed from 3' coterminal subgenomic mRNAs (sgRNAs) (reviewed by Palukaitis and Zaitlin, 1986 In: "The plant virus". M. H. V. van Regenmortel and M. Fraenkel-Conrat, Eds. Vol. 2, pp. 105-131. Plenum Press, NY). Thus, the internal movement protein (MP) gene and the 3'-proximal coat protein gene cannot be translated from genomic RNA of typical tobamoviruses (TMV UI is the type member of the genus *Tobamovirus*). The dicistronic intermediate-length RNA-2 called sgRNA $I_2$ RNA is translated to produce the 30-kDa MP (Bruening et al., 1976 Virology 71, 498-517; Higgins et al., 1976 Virology 71, 486-497; Beachy and Zaitlin, 1977 Virology 81, 160-169; Goelet and Karn, 1982 J. Mol. Biol. 154, 541-550), whereas the 3% proximal coat protein (CP) gene of $I_2$ RNA is translationally silent. This gene is expressed only from the small monocistronic sgRNA (Beachy and Zaitlin, 1977).

It has been shown (Ivanov et al., (1997) Virology 232, 32-43) that, unlike the typical tobamoviruses, the translation of the CP gene of a crucifer-infecting tobamovirus (crTMV) occurs in vitro by an internal ribosome entry mechanism. The genome of crTMV (6312 nts) contains four traditional genes encoding two components of the replicase (proteins of 122-kDa and 178-kDa, the readthrough product of the 122-kDa protein), a 30-kDa MP and a 17-kDa CP (Dorokhov et al., 1993 Dokl. Russian Acad. Sci. 332, 518-52; Dorokhov et al., 1994 FEBS Lett. 350, 5-8). It was found that the 148-nt region upstream of the CP gene of crTMV RNA contains an internal ribosome entry site ($IRES_{CP148}^{CR}$) promoting the internal translation initiation of the CP gene and different reporter genes (Ivanov et al., 1997). By analogy with crTMV, the 3'-proximal CP gene of potato virus X occurs by a mechanism of internal initiation (Hefferon et al., 1997). The capacity of crTMV $IRES^{CR}_{CP}$ for mediating internal initiation of translation distinguishes this tobamovirus from the well-known type member of the genus, TMV U1. The equivalent 148-nt sequence from TMV U1 RNA was incapable ($UI_{CP,148}^{SP}$) of mediating internal initiation of translation (Ivanov et al., 1997).

Recently, it has been shown that the 228- and 75-nt regions upstream of the MP gene of crTMV and TMV U1 RNAs contain IRES elements, $IRES_{MP,75}{}^{CR}$ and $IRES_{MP,228}{}^{CR}$, respectively, which direct expression of 3'-proximal reporter genes from dicistronic constructs in cell-free translation systems and in isolated protoplasts (Skulachev et al., 1999). Moreover, the equivalent sequence from TMV U1 RNA used as the intercistronic spacer ($IRES_{MP,75}{}^{U1}$) was able to mediate translation of the second gene in dicistronic transcripts.

Recent studies on plant viruses also gave new examples of cap-independent initiation of translation without IRES. RNAs of viruses and satellite viruses in the Luteovirus and Necrovirus genera, and the large Tombusviridae family lack both a 5' cap and a 3' poly(A) tail. However, they can be translated efficiently owing to different translation enhancement sequences located in the coding region close to their 3' UTR. These sequences are different from IRES elements in two fundamental ways: they do not confer internal ribosome entry and they are located in the 3' untranslated region (3'UTR). The structure and putative mechanism of action of these sequences are described in details for Barley Yellow Dwarf Virus (BYDV) (Guo et al., 2000 RNA 6, 1808-1820).

IRESes have been identified within some cellular and viral mRNAs of higher eukaryotes (mammals and plants), however, it remains unclear if IRESes do also exist within the mRNAs of lower eukaryotes. Recently, the 5' leader sequences of two yeast mRNAs functioning as IRESs were identified (Zhou et al., 2001 Proc. Natl. Acad. Sci. USA 98, 1531-1536).

The sequences of the animal IRESes characterized are dissimilar (Jackson, 2000, see also FIG. 3) but, in one case, there is evidence of an important role of short nucleotide sequences in IRES functionality of Gtx homeodomain protein. The Gtx IRES contains several non-overlapping segments displaying complementarity to 18 S rRNA that were shown to mediate internal initiation (Hu et al., 1999. Proc. Natl. Acad. Sci. USA 96, 1339-1344). Within one of these segments, a 9-nt GC-rich sequence CCGGCGGGU which is 100% complementary to 18 S rRNA at nucleotides 1132-1124, was identified, and it was shown that synthetic IRESes (FIG. 4) composed of multiple linked copies of this 9-nt IRES module, support internal initiation in animal cells at a very high level (Chappel et al., 2000 Proc. Natl. Acad. Sci. USA 97, 1536-1541).

The low activity of animal viral IRESes (encephalomyocarditis virus IRES, $IRES_{EMCV}$) in plants was reported (Urwin et al., 2000 Plant J. 24, 583-589). So far, there is no evidence for cross-kingdom (plant, animal, yeast) activity of any IRES element. Although the number of nucleotide sequences that are capable of providing cap-independent translation increases constantly, identification of new IRESes has been occasional and accidental, without methodology of prediction. Moreover, the known IRESes do not allow a fine adjustment of efficiency. They are taxonomically limited and structurally highly disparate.

Therefore, it is an object of the invention to provide a method of creating artificial IRES elements.

It is another object to provide artificial IRES elements having cross-kingdom activity.

It is another object of the invention to provide a method of creating IRES elements of a desired degree of efficiency.

It is a further object to provide a process of expressing a nucleotide sequence of interest in eukaryotic cells under translational control of a novel IRES element of the invention.

It is another object to provide a method of identifying nucleic acid elements having IRES activity by searching nucleotide sequences e.g. of data bases.

GENERAL DESCRIPTION OF THE INVENTION

The above objects are solved according to the claims. This invention provides a method of creating a nucleic acid sequence having an adenine-rich nucleic acid block of at least 25 nucleotides in length, whereby said nucleic acid sequence is capable of causing translation of a downstream coding sequence by internal ribosome entry (IRES element).

The inventors of the present invention have surprisingly identified simple criteria for creating nucleic acid sequences which exhibit IRES activity (IRES elements), i.e. sequences which are capable of providing cap-independent translation of a downstream gene or coding sequence by an internal ribosome entry mechanism. The inventors have found that nucleic acid sequences having a block of at least 25 nucleotides with a high adenine content have a high propensity of exhibiting IRES activity in eukaryotic cells. This allows for the first time the creation of artificial IRES elements which are active in eukaryotic cells. Moreover, they surprisingly have cross-kingdom activity, i.e. are active in plant, animal, and fungal cells. An IRES element according to the invention may be tested for (the degree of) IRES activity by:

inserting said IRES element into a linear dicistronic construct between an upstream gene and a downstream GUS reporter gene, whereby said IRES element is positioned for IRES-dependent translation of said downstream GUS gene and whereby said upstream gene is preceded by a stable hairpin structure to prevent IRES-independent translation of said GUS gene;

determining IRES-dependent translation of said GUS gene in a rabbit reticulocyte lysate or in a wheat germ extract in vitro translation assay, whereby GUS gene expression is quantitated preferably relative to a construct having a reference IRES element or a non-IRES element between said upstream gene and said GUS gene; and selecting an IRES element which gives rise to GUS expression in at least one of said in vitro translation assays with the desired efficiency.

This or a similar test may further be used to create an IRES element of a desired activity, which is preferably done by modulating the ratio of the adenine to the pyrimidine nucleotide content. Tests on the activity of an artificial IRES element according to the invention may of course also be carried out in plant or animal cells or in vivo.

Herein, "adenine-rich" or "high adenine content" means a content of adenine that is higher than 30 mol-%. Within this invention, said adenine-rich nucleic acid block has preferably at least adenine-rich if it preferably has at least 40 mol-% adenine. "Pyrimidine-poor" or "low pyrimidine content" means a content of thymine (uracil)+cytidine that is lower than 40 mol-% thymine (uracil)+cytidine.

As to the criteria applied when creating an IRES element according to the invention, a block of at least 25 nucleotides with an adenine content of at least 30, preferably at least 60 and most preferably at least 80 mol-% is provided. The highest IRES activities may be achieved if the adenine content is between 90 and 100 mol-%. The pyrimidine content should preferably be low, i.e. less than 40 mol-%, preferably less than 30 mol-%, and most preferably less than 20 mol-%.

Preferred methods are defined as follows in the order of increasing IRES efficiency:

A method, wherein the adenine-rich nucleic acid block is at least 30 nucleotides long with at least 40 mol-% adenine and less than 40 mol-% pyrimidine.

A method, wherein the adenine-rich nucleic acid block is at least 30 nucleotides long with at least 50 mol-% adenine and less than 30 mol-% pyrimidine.

A method, wherein the adenine-rich nucleic acid block is at least 30 nucleotides long with at least 60 mol-% adenine and less than 20 mol-% pyrimidine.

Any pyrimidine sub-block within said adenine-rich nucleic acid block should preferably be at most 3 nucleotides in length, more preferably at most 2 nucleotides in length. Any sub-block of non-adenine bases separating two adenine bases within said adenine-rich nucleic acid block should preferably have a length of at most 10 bases, more preferably of at most 5 bases. The criteria given above regarding the content of bases of the IRES element of the invention refer to mRNA or to the corresponding coding strand on the DNA level.

There is no strict upper limit for the length of said nucleic acid block. For practical purposes, said block may be chosen to be shorter than 500 nucleotides. It is preferred to create blocks of less than 200 nucleotides. More preferably, said block has between 30 and 100 nucleotides and most preferably it has between 30 to 70 nucleotides. The minimal length of said nucleic acid block is 25 nucleotides. However, its length is preferably at least 40, more preferably at least 50 nucleotides.

Said nucleic acid block according to the invention has a high propensity of conferring IRES activity to a sequence comprising it. The above criteria for creating an artificial IRES element leave many different possibilities to create IRES elements of varying activity. This freedom may be used for fine-tuning IRES activity to a desired level, preferably in combination with an in vitro translation assay.

Whereas this invention focuses on IRES elements made up of a single adenine-rich nucleic acid block, it should be mentioned that 2, 3 or even more adenine-rich nucleic acid blocks may be incorporated in a nucleic acid sequence in order to achieve IRES activity. Such sequences have a particularly high propensity of having strong IRES activity. If 2 or more adenine-rich nucleic acid blocks are used, good IRES activity can be achieved.

Many different approaches may be employed for constructing the IRES element of the invention. Construction is in general performed on the DNA level. An IRES element the sequence of which has been designed according to the principles of the invention may be synthesized by automated DNA synthesis. The complementary strand may be synthesized accordingly. This approach is most suited for IRES elements up to a length of 40 to 100 nucleotides. The designed IRES element may also be synthesized in pieces of suitable length by automated DNA synthesis and annealed after synthesis. These and other methods for construction of a DNA element are known in the art. Of course suitable stretches of DNA may be cut out from longer stretches or from genome sequences.

The invention further provides a process of expressing a nucleotide sequence of interest in eukaryotic cell(s) by introducing into said cell(s) a vector comprising said nucleotide sequence of interest operably linked to an upstream nucleic acid sequence (IRES element) created according to the invention, whereby said nucleotide sequence of interest is translated cap-independently by way of said upstream IRES element.

Said nucleotide sequence of interest may be expressed in a plant or in plant cells. It may also be expressed in an animal or in animal cells. Among animals, mammalian cells or mammals including humans (e.g. for gene therapy) are preferred. Further, said nucleotide sequence of interest may be expressed in fungi, preferably in yeast cells.

The IRES element contained in said vector may be any artificial IRES element created according to the invenion. It may e.g. be the $(GAAA)_{16}$ or the poly(A) IRES element as specifically disclosed in the examples or functionally equivalent IRES elements. Further examples of artificial IRES elements are shown in FIGS. 5, 6, 10, and 12 to 19 (see also examples). Said process of expressing does not comprise use of known or natural IRES elements. Particularly, it does not comprise use of known viral IRES elements.

Said nucleotide sequence of interest may be expressed from monocistronic mRNA. However, the high potential of IRES technology is in bicistronic or polycistronic expression, which allows to express all subunits of a protein complex or a whole biochemical cascade or pathway. Therefore, said nucleotide sequence of interest is preferably expressed from a bicistronic or polycistronic mRNA.

Said eukaryotic cells or eukaryotic organisms may be stably transformed or transiently transfected with said vector. Methods of transforming or transfecting animal or plant cells are well-known in the art. Various methods can be used to deliver a DNA or RNA vector into a plant cell, including direct introduction of said vector into a plant cell by means of microprojectile bombardment, electroporation or PEG-mediated treatment of protoplasts (for review see: Gelvin, S. B., 1998, *Curr. Opin. Biotechnol.*, 9, 227-232; Hansen & Wright, 1999, *Trends Plant Sci.*, 4, 226-231). Plant RNA and DNA viruses are also efficient delivery systems (Hayes et al., 1988, *Nature*, 334, 179-182; Palmer et al., 1999, *Arch. Virol.*, 144, 1345-1360; Lindbo et al., 2001, *Curr. Opin. Plant. Biol.*, 4, 181-185). Said vectors can deliver a transgene either for stable integration into the genome/plastome of the plant (direct or *Agrobacterium*-mediated DNA integration) or for transient expression of the transgene ("agroinfiltration"). Similarly, animal cells may be electroporated, infected by viral vectors or transfected using Lipofectin.

Construction of the vectors for the expression process of the invention may be done according to standard procedures of molecular biology. The IRES elements of the invention are placed upstream of said nucleotide sequence of interest in said vector for IRES-dependent translation of said nucleotide sequence of interest. Specific embodiments are given in the figures and in the examples section.

The invention comprises transgenic or transiently modified eukaryotic cell(s) containing a nucleic acid sequence (IRES element) created according to the invention and operably linked to a nucleotide sequence of interest.

The invention further comprises a vector containing an IRES element created according to the invention and an expression cassette containing said IRES element for constructing the vector of the invention. Said vector may be an RNA vector containing an IRES RNA sequence, as well as a DNA vector containing a cDNA copy of a novel IRES RNA sequence.

The invention is useful, as it allows one skilled in the art to create artificial translational elements with IRES activity. It allows to identify IRES elements that are more active than previously described ones. In addition, it allows creation or identification of IRES elements that are universal with cross-kingdom activity and have taylor-made activity.

BRIEF DESCRIPTION OF THE FIGURES

FIG. 3. Nucleotide sequences of known IRESes.

DETAILED DESCRIPTION OF THE INVENTION

Figure 1:
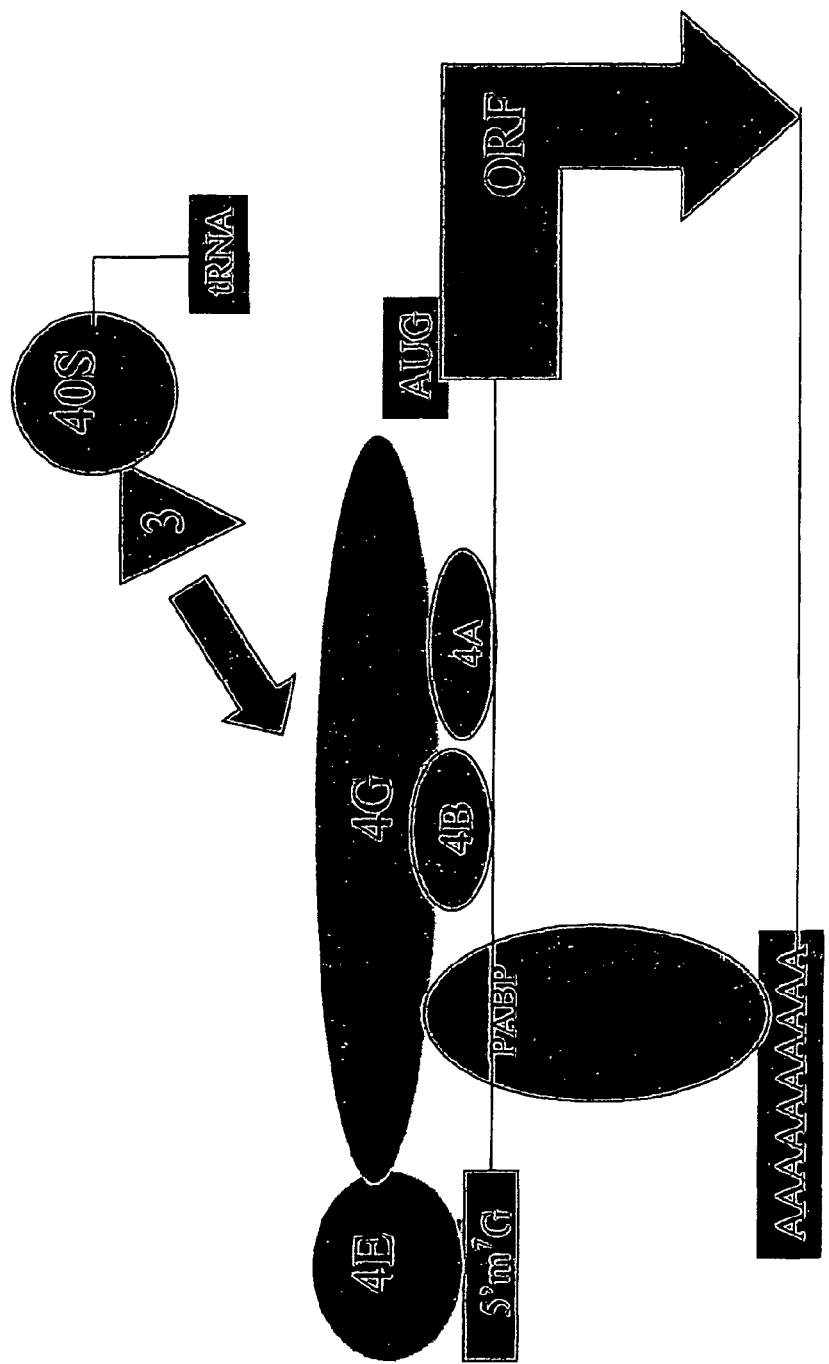
FIG. 1. Simplified model of canonical eukaryotic cap-dependent translation initiation. The eIF4E-eIF4G interaction targets the small ribosomal subunit to the 5' end of the mRNA. The eIF4G also interacts with Pab1p, eIF3, and the RNA helicase eIF4A to mediate the initiation process. ORF: open reading frame; PABP: poly (A)-binding protein.
Figure 2:
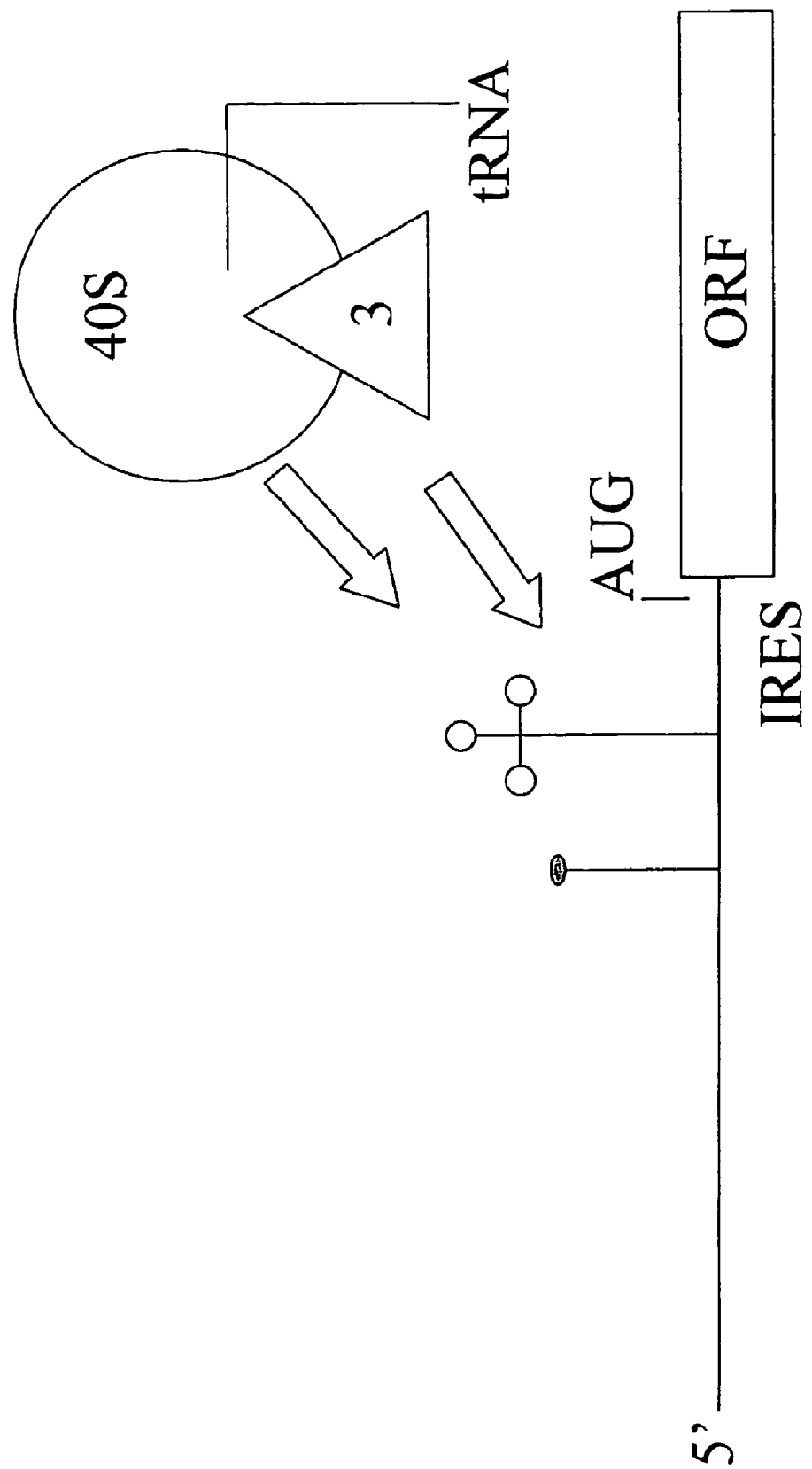
FIG. 2. Simplified model mechanism of ribosome recruitment to mRNA during hepatitis C virus IRES-mediated translation initiation. The IRES element bypasses the need for an eIF4E-eIF4G interaction by providing alternative means by which the ribosome is recruited to the mRNA. Arrows indicate the various direct interactions between IRES elements and the initiation 40 S complex.
Figure 4:
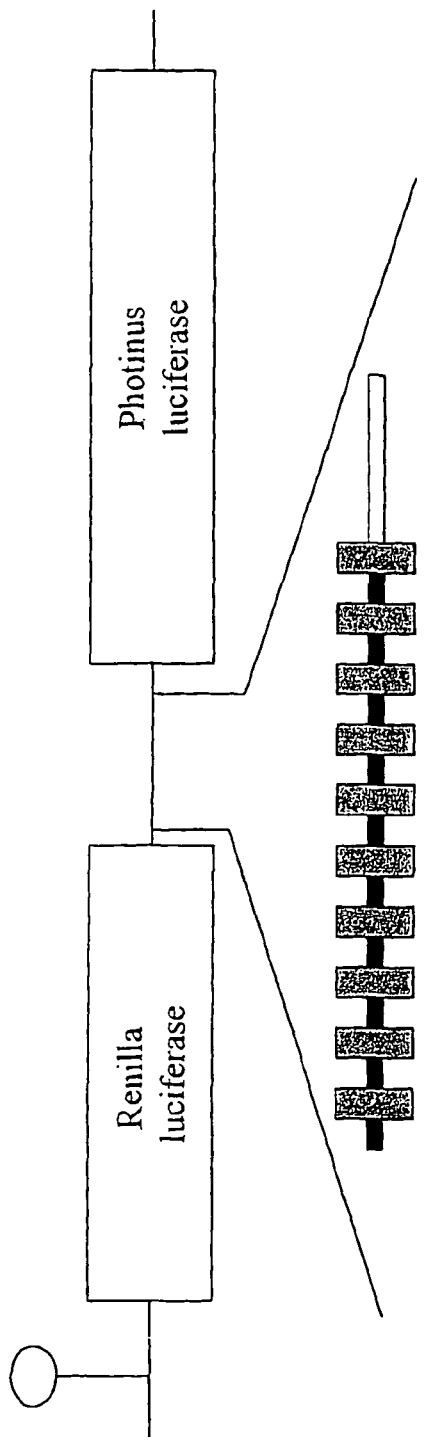
FIG. 4 depicts dicistronic mRNA containing synthetic IRES based on multiple linked copies of CCGGCGGGU of the Gtx 5'UTR (Chappel et al., 2000. Proc. Natl. Acad. Sci. USA 97, 1536-1541).

There are several inventions which describe IRES elements that were used for cap-independent expression of foreign gene(s) in linear multicistronic mRNA in mammalian cells (U.S. Pat. No. 6,060,273; U.S. Pat. No. 6,114,146; U.S. Pat. No. 5,358,856; U.S. Pat. No. 6,096,505; U.S. Pat. No. 171, 821; U.S. Pat. No. 5,766,903), plant cells (WO98/54342) and, generally, in eukaryotic cells (U.S. Pat. No. 171,821; U.S. Pat. No. 5,766,903; U.S. Pat. No. 5,925,565; U.S. Pat. No. 6,114, 146). Also, circular RNA was developed to provide cap-independent IRES-mediated expression of a gene (U.S. Pat. No. 5,766,903). Cap-independent translation of eukaryotic mRNA could be mediated by a translation enhancement sequence taken from barley yellow dwarf virus RNA which is principally different from known IRESes (U.S. Pat. No. 5,910,628). Generally, all published inventions in the field describe natural IRESes isolated from animal (see, for example, U.S. Pat. No. 5,358,856) or plant viruses (WO98/54342) without addressing the question for their cross-kingdom activity, i.e. the activity of known IRESes is limited to either animal or plant cells. No approaches for the creation of non-natural, artificial IRESes that are capable of providing efficient cap-independent foreign gene expression in animal and plant cells have been described. Furthermore, there are no approaches available of creating or identifying new IRES elements having cross-kingdom activity.

WO01/55369 describes the creation of synthetic IRES elements based on natural IRES element fragments interacting with 18 S ribosomal RNA. However, the approach is limited to identifying IRES elements functional in animal systems. In addition, chimeric dicistronic constructs that were proposed in this invention were not analyzed to rule out the possibility that the GC-rich intercistronic putative IRES element functions as a transcriptional promoter, thereby producing a monocistronic mRNA from which the cistron was actually translated (Kozak, 2001 *Mol. Cell. Biol* 21, 1899-1907). Without having ruled out this and other alternative explanations, the authors concluded that the Gtx-derived sequence was an IRES. They postulate that IRES activity results from base pairing between mRNA and rRNA, citing as evidence the ability of the CCGGCGGGU element to be photochemically cross-linked to 18 S rRNA (Hu et al., 1999, *Proc. Natl. Acad. Sci. USA* 96, 1339-1344). This cross-linking, however, may well be unrelated to the putative IRES function, as it did not require formation of a ribosome-mRNA initiation complex. Indeed, cross-linking occurred even when the Gtx-derived sequence was incubated with deproteinized 18 S rRNA.

In contrast to WO01/55369, the possibility of transcriptional promoter activity of the IRESs of the present invention was investigated. It was proven by Northern blotting that the artificial IRES elements of this invention used in dicistronic assays do not act as transcriptional promoters. Further, evidence showing that polypurine (A)-rich sequences (PARS) do not act as promoters in plant cells comes from experiments with transgenic plants expressing PARS-rich $IRES_{CP,148}^{CR}$ (Dorokhov et al. 2002. Proc. Natl. Acad. Sci. USA 99, 5301-5306).

Contrary to known technologies, the present invention provides the principles for the creation of artificial IRESes which may be easily synthesized according to methods known in the art. These IRESes should preferably have a high level of cross-kingdom activity in eukaryotic cells, including fungal (e.g. yeast), mammalian and plant cells. Moreover, owing to the fact that IRESes of the invention have similarity to prokaryotic ribosome binding sites (RBS) of bacteria e.g. *E. coli* as functional analogs of eukaryotic IRESes, the artificial IRESes of the invention are active in prokaryots as well as chloroplasts and mitochondria.

Figure 7:
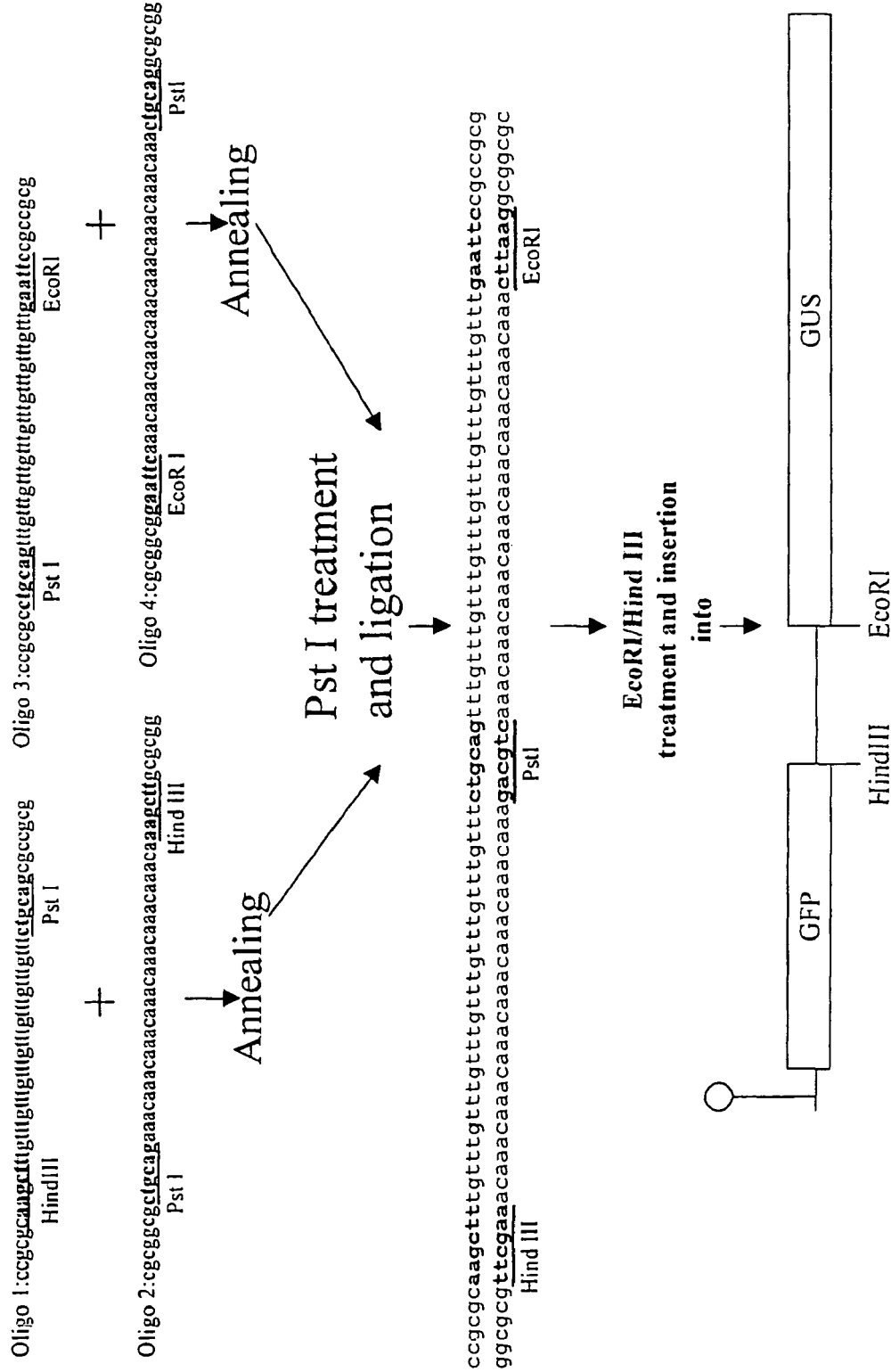
FIG. 7 depicts nucleotide primer sequences and cloning steps of an artificial sequence containing 16 copies of the GUUU element. Restriction sites are underlined. Oligos 1 to 4 correspond to SEQ ID NOS:25 to 28, respectively. The coding and complementary strands of said IRES correspond to SEQ ID NOS:29 and 30, respectively.

For testing an IRES element created according to the invention, a test system was deviced comprising the bicistronic DNA construct "H-GFP-GUS" having the following elements in this order: a structure that forms a stable hairpin (H) on the mRNA level, a green fluorescent protein (GFP) gene (GFP coding sequence), an intercistronic spacer with restriction site(s) for inserting potential IRES elements, and the GUS gene (GUS coding sequence). A potential IRES element is inserted into the spacer between GUS and GFP. This construct is then transcribed in vitro using e.g. T7 RNA polymerase to obtain mRNA. The obtained mRNA is then translated in vitro using a rabbit reticulocyte lysate (RRL) or a wheat germ extract (WGE) in vitro translation system. Both in vitro translation systems are commercially available e.g. from Promega and from Roche Diagnostics and may be used according to the manufacturer's instructions. After translation, GUS expression is determined e.g. via its enzymatic activity and a colorimetric detection, by autoradiography, or by Western blotting. GUS gene expression is quantitated preferably relative to a construct having a reference IRES element or a non-IRES element between said upstream gene and said GUS gene. As a reference IRES element having strong IRES activity said poly(A) nucleic acid block (see examples) may be used. As a non-IRES element, said poly(G) nucleic acid block (see examples) or the nucleic acid blocks depicted in FIG. 7, 8 or 9 may, for example, be used.

Said hairpin structure in said bicistronic DNA construct prevents cap-dependent translation, such that all GUS expression can be ascribed to the translational activity of the potential IRES element inserted in said intercistronic spacer of said construct. Said hairpin has to be stable enough to efficiently prevent cap-dependent translation. Preferably, its stability is higher than 30 kcal/mol (see Kozak, M. (1986) Proc. Natl. Acad. Sci. USA 83, 2850-2850). Insufficient stability of said hairpin may be recognized by any expression of said GFP gene. GFP translation may be detected e.g. by way of its fluorescence, by Western blotting or by autoradiography.

The H-GFP-GUS construct used herein was built from plasmid pBluescriptll SK+, a GUS nucleotide sequence and a GFP sequence (Example 1). The hairpin structure has the sequence: ggtaccgggcccccccctcgaggtcgacg-gtatcgataccgtcgacctcgaggggggcccggtacc (SEQ ID NO:60). Equivalent structures can be easily created by a person skilled in the art.

All aspects in connection with the in vitro translation systems are well studied and known in the prior art. Details can be found in the following documents and in references cited therein: Anderson, C., et al. (1985) Meth. Enzymol. 101, 635; Krieg, P. and Melton, D. (1984) Nucl. Acids Res. 12, 7057; King, R. W. et al. (1997) Science 277, 973; DiDonato, J. A. and Karin, M. (1993). Promega Notes 42, 18; Pelham, H. R. B. and Jackson, R. J. (1976) Eur. J. Biochem. 67, 247; Jackson, R. J. and Hunt, T. (1983) Meth. Enzymol. 96, 50; Technical Bulletins from Promega Corp. No. 126 and No. 165 and Technical Manual No. 232 from the same company.

Potential IRES elements which give rise to GUS gene expression in such a WGE or RRL translation assay are IRES elements according to the invention. The IRES elements created or identified according to the invention typically exhibit cross-kingdom activity, i.e. they can be used to express a gene of interest under translational control of said IRES in plants and in animals. In spite of said cross-kingdom activity, the activity of said IRES element is normally not the same when expression of a gene of interest is compared in plant or animal systems. Variations in expressions levels naturally exist between the two in vitro translation systems mentioned above. In in vivo systems, these variations are in general even higher. Still, the IRES elements of this invention show surprisingly high IRES activity in both in vitro systems, in plant cells and in animal cells.

This invention further provides a method of identifying nucleic acid elements having IRES activity by searching nucleotide sequences, notably nucleotide sequences of genome data bases, applying the above-described group of criteria.

Said searching may be carried out on any known nucleotide sequence and on sequences that will become known in the future. Nucleotide sequences of eukaryotic origin, i.e. plant and animal sequences are preferably searched and those of higher plants or higher animals are most preferred.

Whole genome sequences including nuclear genomes and organelle genomes like plastid or mitochondrial genomes may be searched. Eukaryotic nuclear genome sequences are preferred. Searching may be carried out on DNA or on RNA sequences. If double-stranded DNA is used, both strands may be screened. The coding strand is screened preferentially. The searching may be restricted to 5' UTR sequences of genes. It is equivalent to screen 5' UTR sequences on the mRNA level.

Searching may be carried out, in the simplest case, by eye by scanning along printed or written nucleotide sequences. This approach can be successful, especially if one focuses on 5' UTR sequences. It is more convenient to employ an automatic screening method e.g. by using a computer and a suitable computer program. In this way, large data bases of nucleotide sequences may be screened with the potential of finding many IRES elements.

The invention therefore comprises the use of a computer and a computer program for the above-described searching for IRES elements in nucleotide sequences. Said computer program comprises an algorithm based on the group of criteria as defined in the claims.

One essential advantage of the present invention is the possibility to express two or more genes in multicistronic cassettes in plant cells either transiently or via stable transformation (transgenic plants).

Another advantage of the present invention is the possibility to express two or more genes in multicistronic cassettes in human or other mammalian cells via transient or stable transformation (transgenic animals).

A further advantage of the present invention is the possibility to express two or more genes in multicistronic cassettes in yeast cells.

A further advantage of the present invention is the possibility to create viral vectors for expressing a foreign gene via adenine-rich IRESes in mammalian and especially in human cells.

Another preferred embodiment of this invention is the creation of new IRESs on the basis of eukaryotic mRNA 5'-UTR containing AGNB(s). Our analysis of 5'-UTRs of heat shock protein (HSF) mRNAs revealed adenine-rich 5' leaders. Moreover, experimental testing of the *Nicotiana tabacum* heat shock factor (NtHSF) mRNA leader confirmed this prediction. NtHSF 5'-UTR turned out to have IRES activity not only in plant but also in human cells. This invention provides 5' non-translated regions of eukaryotic mRNA that contain adenine-rich sequences as IRESes for the expression of several genes in multicistronic cassettes in plant or animal cells either transiently or via stable transformation (transgenic organisms). Moreover, such IRESs might be used for expression of foreign and natural genes in animal virus-based vectors e.g. in gene therapy.

In the following, the invention will be further described using specific examples. Standard molecular biological techniques were carried out according to Sambrook et al (1989, Molecular Cloning: a Laboratory Manual. $2^{nd}$ edn. Cold Spring Harbor, N.Y.). All plasmids utilized in the invention can be prepared according to the directions of the specification by a person of ordinary skill.

Example 1

A Method of Creating Non-Natural, Artificial IRESes Containing an Adenine-Rich Nucleotide Block In this example it is shown that it is possible to create artificial IRES elements having an adenine-rich nucleotide block.

Cloning strategy: Bacteriophage T7 transcriptional promoter- and 35 S-based bicistronic plasmids of the series H-CP-ICS-GUS or CP-ICS-GUS, wherein crTMV CP gene expression as a 5' proximal cistron is blocked by a stable artificial hairpin (H) structure. On the contrary, GUS gene expression is under the control of an intercistronic sequences (ICS) including a synthetic polylinker-based sequence (72 nts of length), $IRES_{MP,228}^{CR}$, $IRES_{MP,75}^{CR}$ and $IRES_{CP148}^{CR}$, $UI_{CP,148}^{SP}$, and $IRES_{CP148}^{UI}$ which have been described previously (Ivanov et al., 1997; Skulachev et al., 1999). Construction of H-GFP-ICS-GUS plasmids was as follows. The construct pH-Cla was obtained by cloning of the pBluescript SK+ (Stratagene) polylinker (PL) fragment into the same vector. The fragment was excised from SK+ by ClaI and KpnI (KpnI was blunted with T4 DNA polymerase) and cloned back into the SK+ vector using ClaI and SmaI sites. Then, a polylinker BamHI-SacI fragment from plasmid pGEM-3Z was cloned into pH-Cla by BamHI and SacI sites yielding vector phClaPoly. This vector contained two inverted 45-nt repeats followed by multiple cloning sites. At the next stage, plasmid phGFP was obtained by cloning the GFP gene into plasmid pH-ClaPoly by BamHI and Hind III sites (the GFP gene was obtained as a PCR product using ccggatccttatggt-gagcaagggcgaggag (SEQ ID NO:61) and cgcaagcttacttgta-cagctcgtccatg (SEQ ID NO:62) oligonucleotides and plasmid GFP-241 (Solovyev et al., 1999) as a template. To obtain pH-GFP-IRES$_{CP,148}^{CR}$-GUS, the EcoRI-SacI fragment from plasmid pH-CP-IRES$_{CP,148}^{CR}$-GUS (Skulachev et al., 1999) was cloned into vector phGFP using EcoRI and SacI sites. Plasmid pH-GFP-PL-GUS was obtained by digesting pH-GFP-IRES$_{CP,148}$-GUS with EcoRI and NcoI enzymes, filling protruding ends with Klenow fragment followed by self-ligation of the plasmid. As a result, this plasmid contains GFP and GUS genes with HindIII, SmaI, KpnI and EcoRI sites in between.

Figure 5:
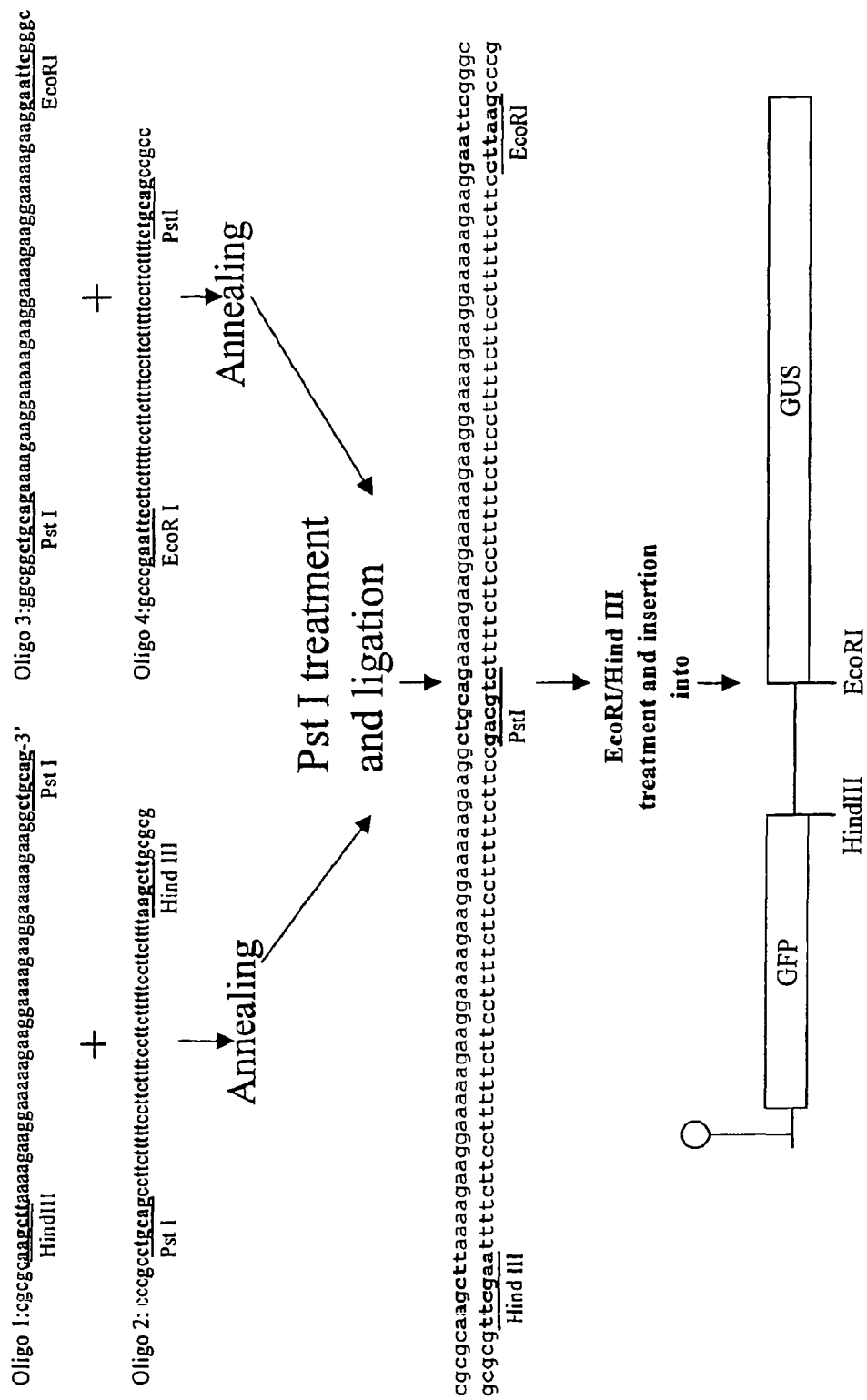
FIG. 5 depicts nucleotide primer sequences and cloning steps of an artificial IRES containing four copies of Ecp elements. Restriction sites are underlined. Oligos 1 to 4 correspond to SEQ ID NOS:13 to 16, respectively. The coding and complementary strands of said IRES correspond to SEQ ID NOS:17 and 18, respectively.

To produce a non-natural, artificial IRES having an adenine-rich nucleotide block, two pairs of oligonucleotides were annealed to each other (see FIG. 5). The obtained DNA fragments were digested with PstI restrictase and ligated to each other. The ligated fragments were isolated using agarose electrophoresis and digested with HindIII and EcoRI restrictases. Plasmid pH-GFP-PPx4-GUS was obtained by cloning the PPx4 fragment into the pH-GFP-PL-GUS vector using HindIII and EcoRI sites.

In vitro translational assays: WGE and RRL translation assay were carried out as described in Technical Bulletin No. 165 and No. 126, respectively, from Promega Corporation using the coupled transcription/translation systems of catalogue numbers L4140 and L4610, respectively. Alternatively, a conventional RRL system from Promega, catalogue number L4960 (Technical Manual No. 232) was employed. Linear H-GFP-GUS vectors having potential IRES elements inserted between GFP and GUS were transcribed using the T7 promoter/RNA polymerase system. RNA transcripts were precipitated with LiCl, dissolved in water, and reprecipitated with ethanol. RNA concentrations were measured by spectrophotometry and 5 µg of transcript was taken for 25-µl in vitro translation sample. GFP and GUS expression were detected by autoradiography.

Transient assay system of plant protoplasts The following procedures of protoplasts preparation and transfection were used: (i) The protoplasts were isolated from *N. tabacum* (cv. W38) leaves as described (Saalbach et al., 1996 Plant Physiol. 112, 975-985). Aliquots of $4 \times 10^5$ protoplasts were transfected with 30 µg of pFF19-based dicistronic DNA constructs "GFP-spacer-GUS" and incubated for 36 hours at 25° C. in the dark. GUS activity was measured as relative light units (RLU). GUS activity was determined according to (Jefferson 1987. Plant Mol. Biol. Rep. 5, 387-405) using MUG. For each experiment background GUS activity associated with non-transfected protoplasts was subtracted. Protein concentrations were estimated using the Bio-Rad protein assay kit based on the method of Bradford (1976 Anal. Biochem. 72, 248-254). GFP expression was detected with Western-blot analysis using monoclonal mouse antibodies (Boehringer Mannheim No 1814460) according to the manufacturer's manual. GFP amounts in western-blot bands were calculated using Bio-Rad Quality-One software.

Transfection of HeLa Cells Using Vaccinia Virus and T7 Promoter Containing Plasmids Encoding GUS HeLa cell monolayers were grown on 3.5 cm Petri dishes in Dulbecco's modified minimal essential medium supplemented with 10% heat-inactivated fetal calf serum and 100 units/ml streptomycin and penicillin. Virus stocks of modified vaccinia virus Ankara (MVA) expressing the bacteriophage T7 RNA polymerase gene were prepared according to usual methods. HeLa cell dishes that were 80-90% confluent were infected with virus using 30-40 pfu/cell. After a 45 min absorption period the cells were washed and transfected using Opti-MEM (Life Technologies, Inc.) plasmid DNA and Lipofectin (life Technologies, Inc.). A transfection mixtures of 2 µg DNA in 5 µl Lipofectin was used for a 3.5 cm plate. For each construct, 6 plates were used in each experiment. Cells were incubated at 37° C. for 6 h. After incubation the media was removed, cells were washed twice with PBS and lysed directly on the plate in 250 µl lysis buffer (100 mM KHPO$_3$ pH 7.8, 0.2% Triton X-100, 0.5 mM DTT) for 10 minutes. The lysate was collected, clarified by centrifugation at 2000 g for 10 minutes and stored at -70° C. GUS activity was detected in 20 µl of lysate using GUS Light™ reagent system (Tropix, MA, USA) according to the manufacturer's protocols.

Example 2

A Method of Creating Non-Natural, Artificial IRES Containing 16 Copies of the GAAA Element The main goal of this example is to demonstrate the possibility to create a non-natural, artificial IRES element having an adenine-rich nucleic acid block of 16 copies of the GAAA sequence, whereby the A and the G nucleotide contents are 75% and 25%, respectively.

Cloning Strategy

Figure 6:
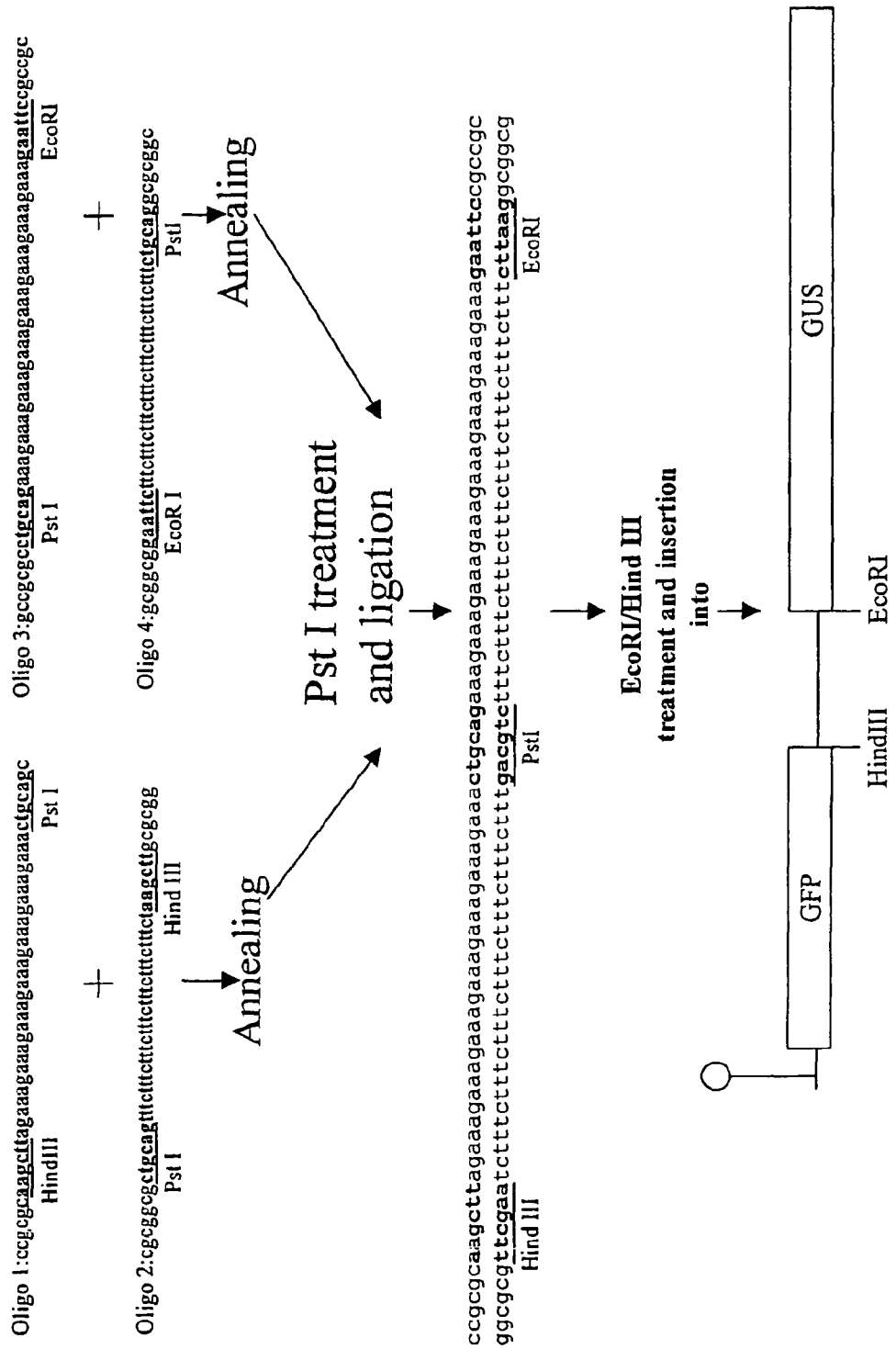
FIG. 6 depicts nucleotide primer sequences and cloning steps of an artificial IRES containing 16 copies of the GAAA element. Restriction sites are underlined. Oligos 1 to 4 correspond to SEQ ID NOS:19 to 22, respectively. The coding and complementary strands of said IRES correspond to SEQ ID NOS:23 and 24, respectively.
Figure 8:
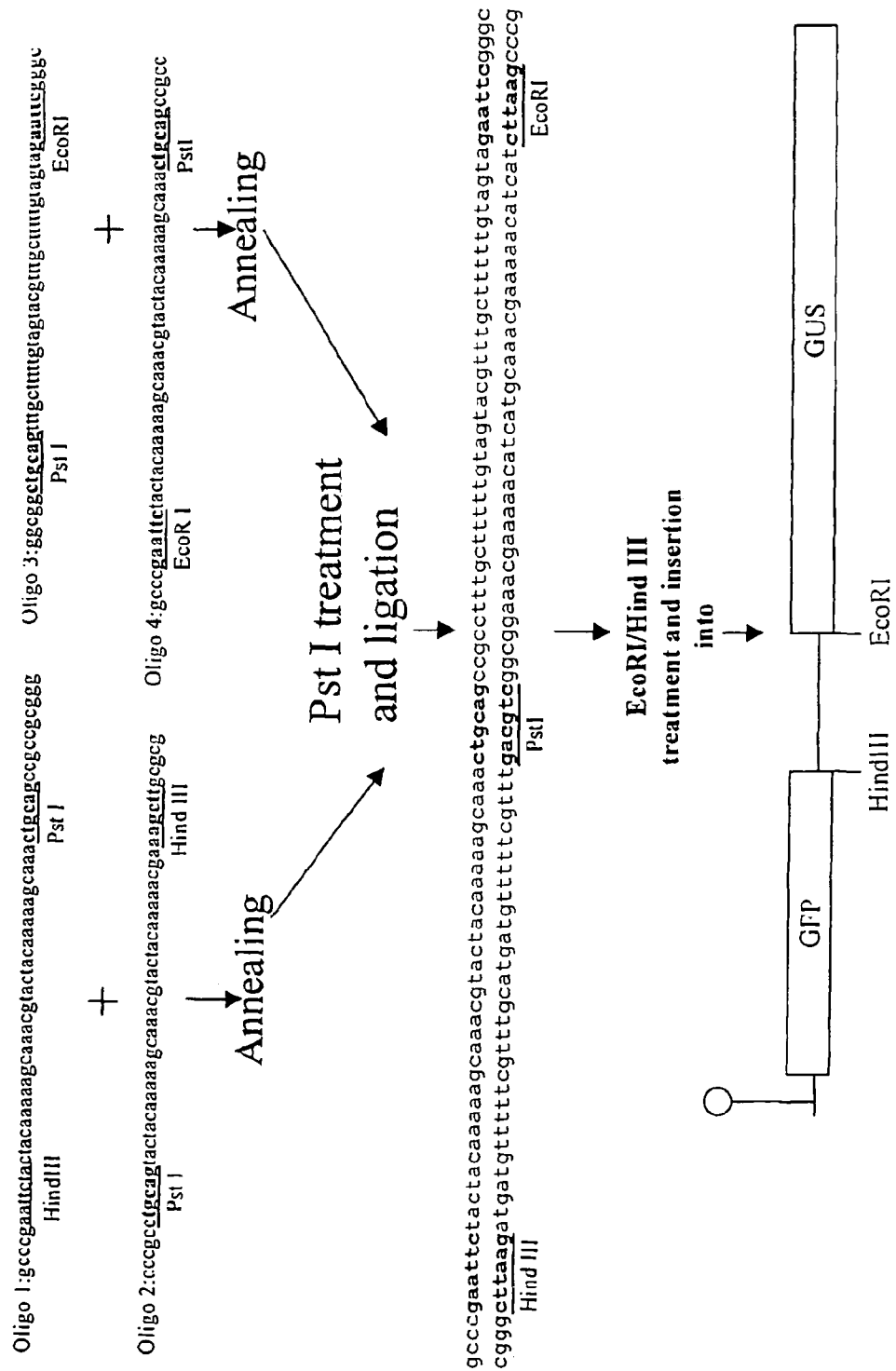
FIG. 8 depicts nucleotide primer sequences and cloning steps of an artificial sequence containing 4 copies of the uuugcuuuuuguagua element (SEQ ID NO:31, Emp x 4). Restriction sites are underlined. Oligos 1 to 4 correspond to SEQ ID NOS:32 to 35, respectively. The coding and complementary strands of said IRES correspond to SEQ ID Nos:36 and 37, respectively.
Figure 9:
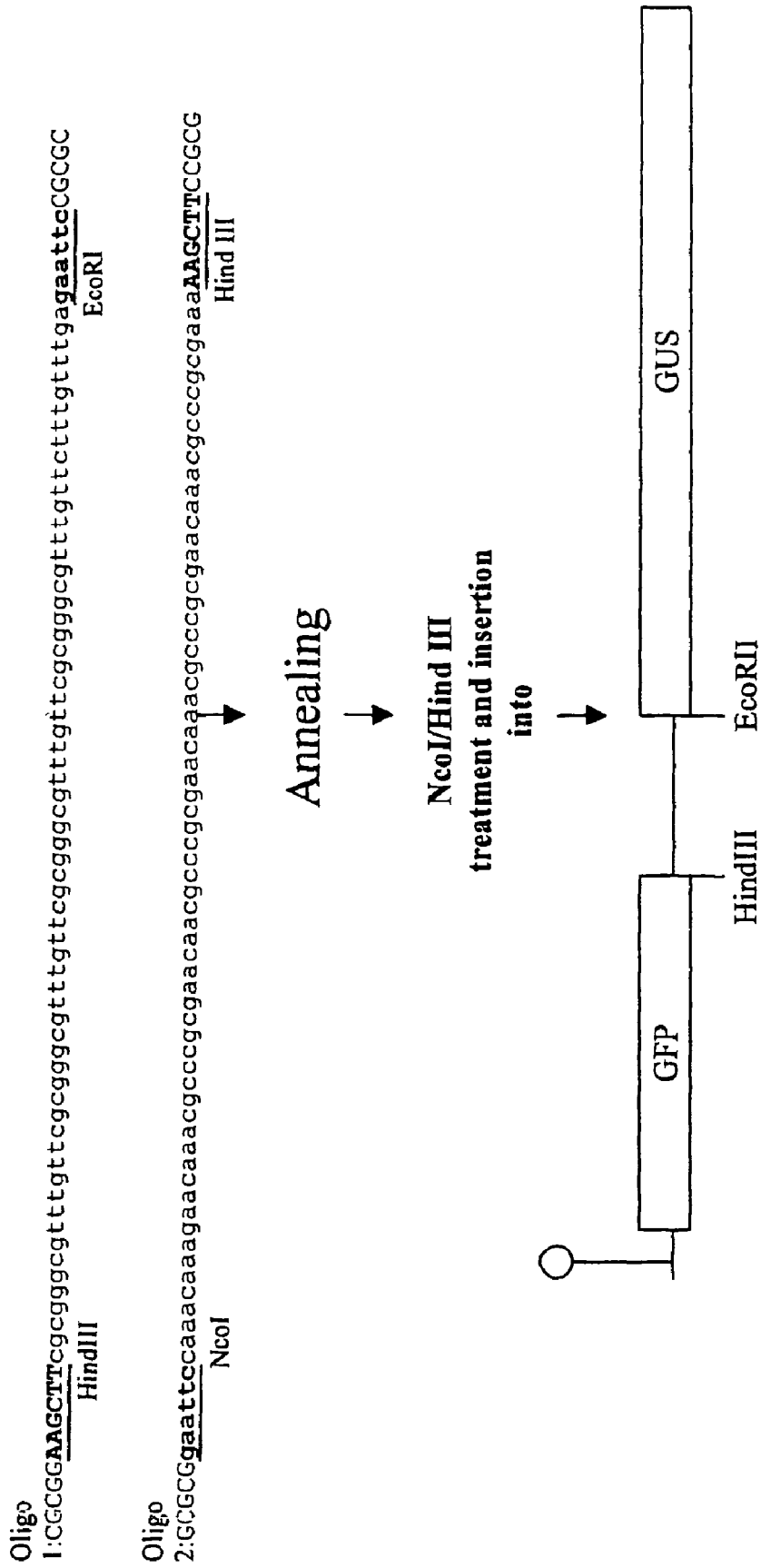
FIG. 9 depicts nucleotide primer sequences and cloning steps of an artificial sequence containing a GCU-rich element. Restriction sites are underlined. Oligos 1 and 2 correspond to SEQ ID NOS:38 and 39, respectively
Figure 10:
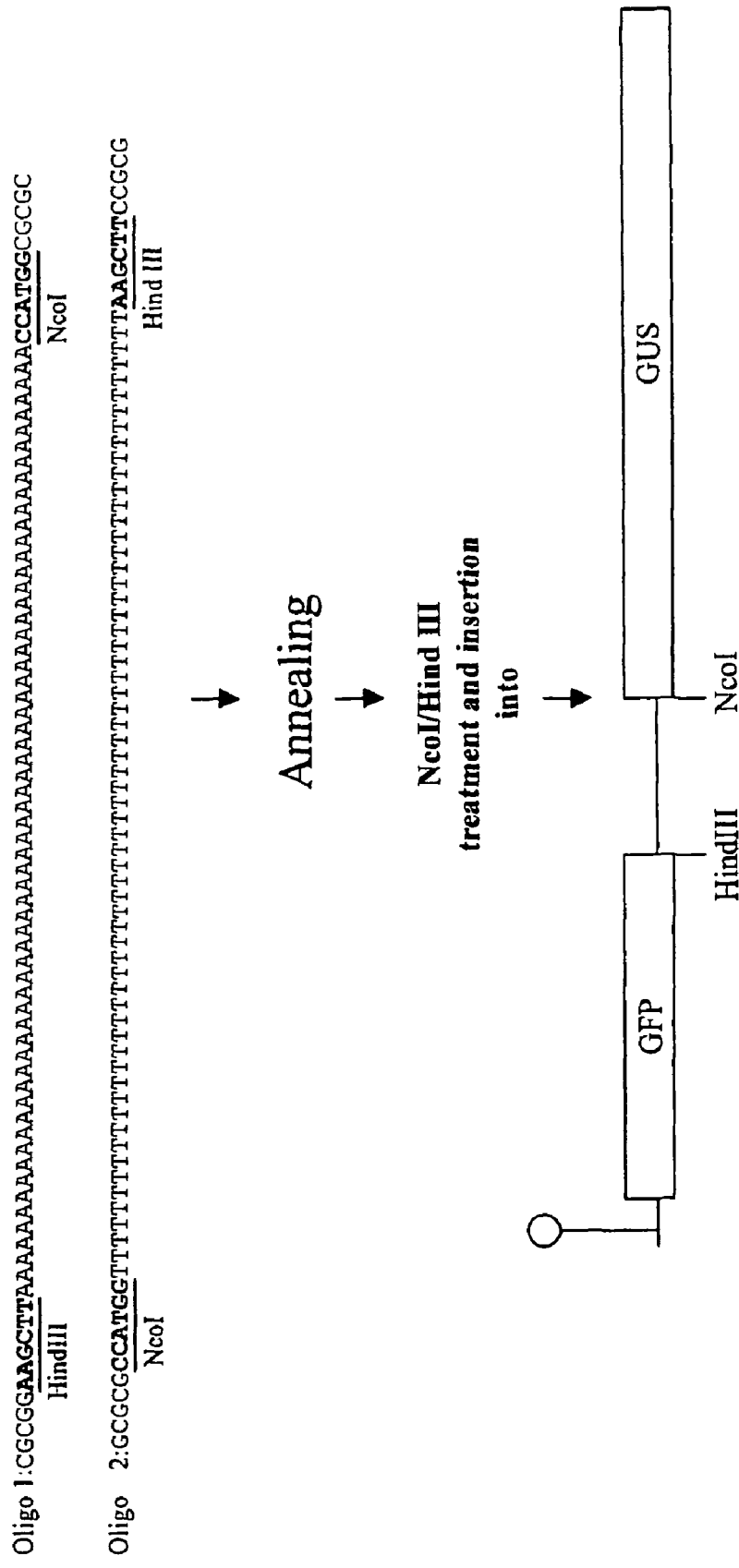
FIG. 10 depicts nucleotide primer sequences and cloning steps of an artificial IRES containing a poly(A) sequence. Restriction sites are underlined. Oligos 1 and 2 correspond to SEQ ID NOS:40 and 41, respectively.

To produce a non-natural, artificial IRES containing multiple copies of the GAAA sequence, two pairs of oligonucleotides were annealed (see FIG. 6). The obtained DNA fragments were digested with PstI restrictase and ligated to each other. The ligated fragments were isolated using agarose electrophoresis and digested with HindIII and EcoRI restrictases. Plasmid pH-GFP-(GAAA)$_{16}$-GUS was obtained by cloning of the (GAAA)$_{16}$ (SEQ ID NO:63) fragment into the pH-GFP-PL-GUS vector using HindIII and EcoRI sites (FIG. 6). Cloning steps of artificial sequences containing 16 copies of the GUUU element, four copies of the UUUGCUUUUU-GUAGUA (SEQ ID NO:31) element and a GCU-rich sequence used as negatives controls are shown in FIGS. 8-10, respectively.

Approaches for testing artificial IRESes are described in Example 1.

Example 3

A Method of Creation of Non-Natural, Containing a Poly(A) Nucleic Acid Block

The main goal of this example is to test the possibility to create a non-natural, artificial IRES containing a poly(A) sequence with an A nucleotide contents of 100%. This sequence was compared to a poly(G) sequence with a G content of 100%. The main result of these examples is that an artificial sequence containing the poly(A) sequence does function as an IRES, whereas the artificial sequence containing the poly(G) sequence does not.

Figure 11:
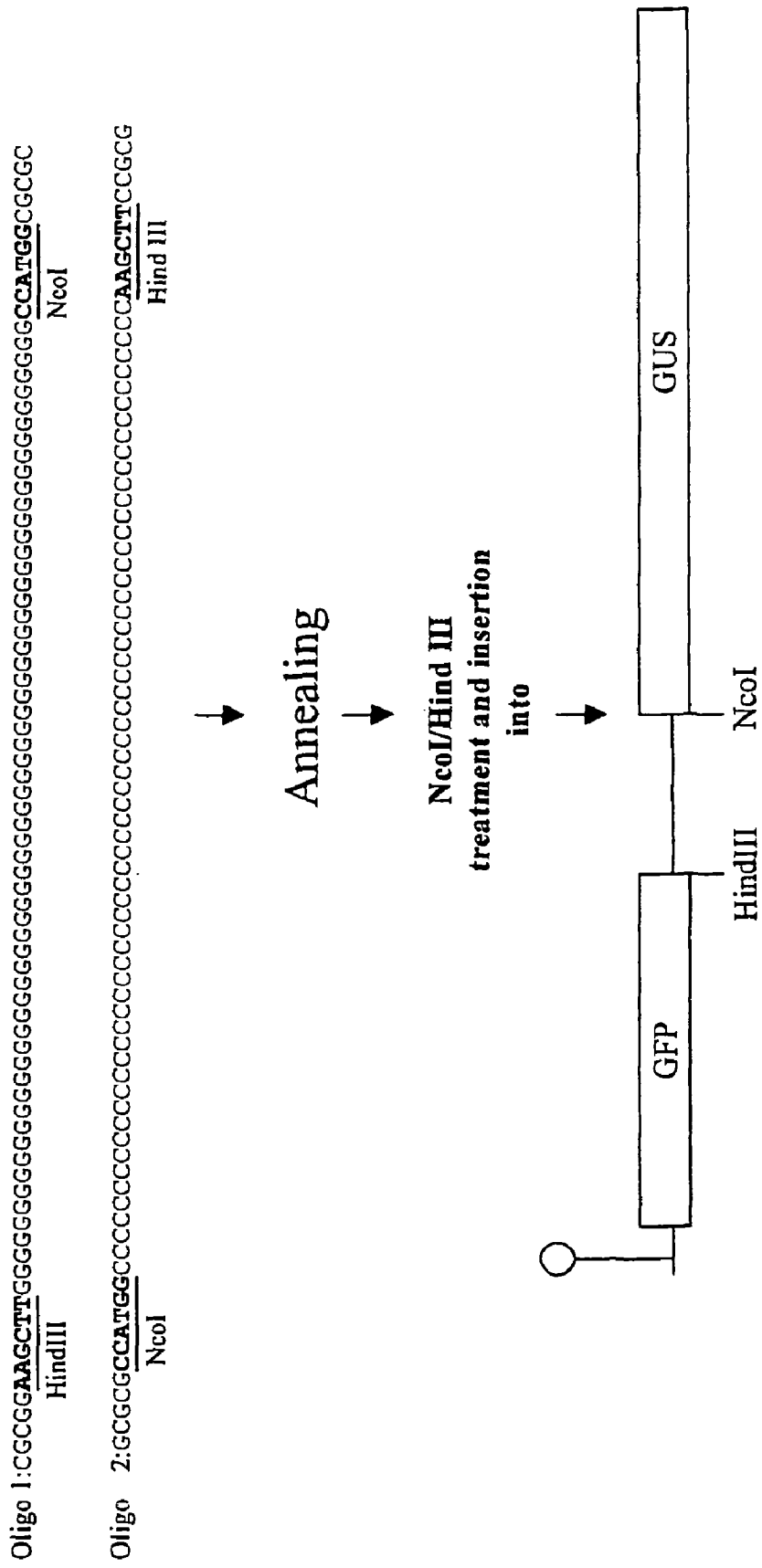
FIG. 11 depicts nucleotide primer sequences and cloning steps of an artificial poly(G) sequence. Restriction sites are underlined. Oligos 1 and 2 correspond to SEQ ID NOS:42 and 43, respectively.

Cloning strategy of the poly(A)-containing IRES and of the poly(G) sequence are presented in FIGS. 10 and 11, respectively. Approaches for testing of the obtained constructs are described in Example 1.

Example 4

Creation of Non-Natural, Artificial Adenine-Rich Sequences Containing Different Guanine and Pyrimidine Base Contents The main goal of this example is to test the possibility to create non-natural, artificial IRES elements containing adenine-rich sequences, whereby the adenine contents vary between 100 and 25% and the pyrimidine nucleotide contents are up to 20%.

Figure 12:
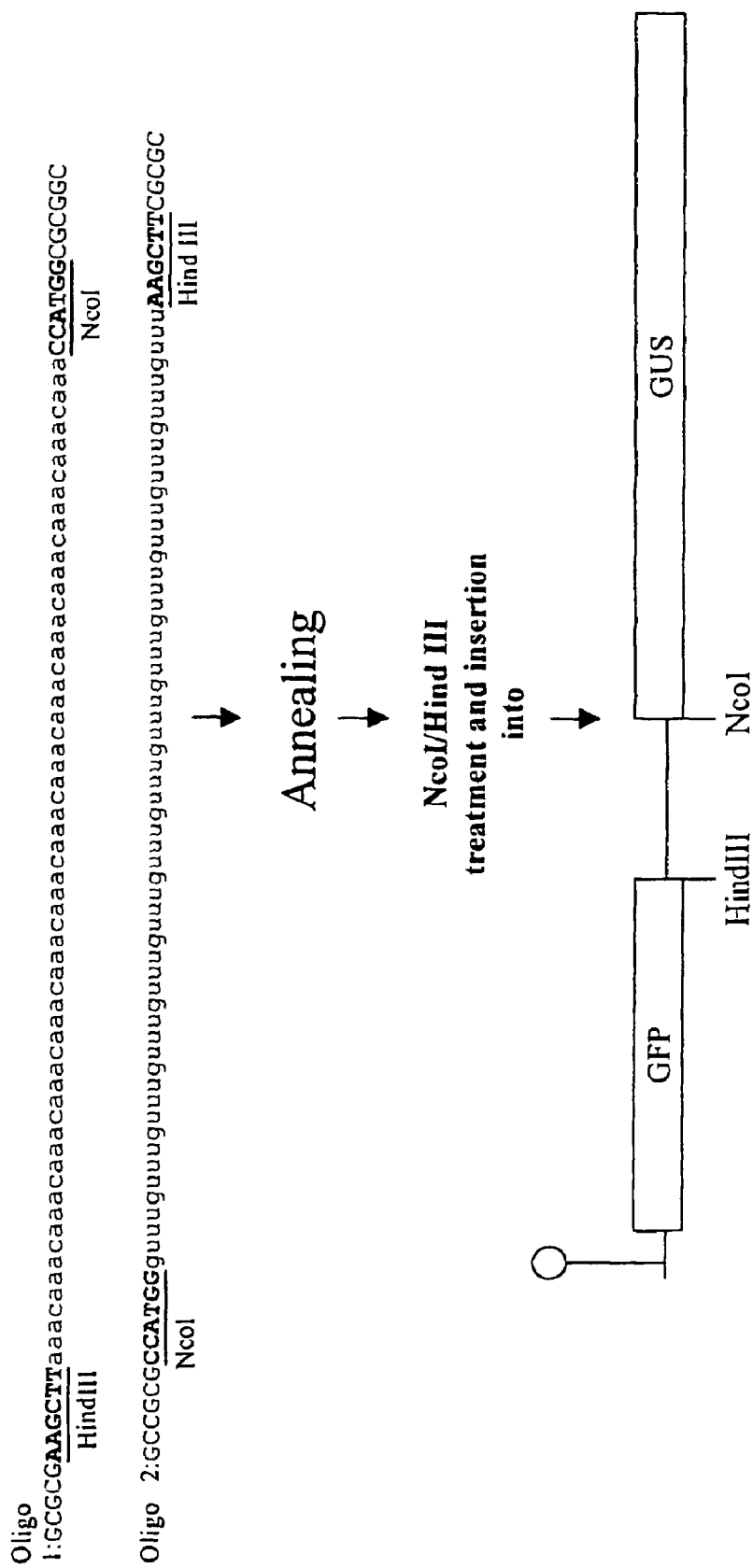
FIG. 12 depicts nucleotide primer sequences and cloning steps of an artificial IRES containing 16 copies of the AAAC element. Restriction sites are underlined. Oligos 1 and 2 correspond to SEQ ID NOS:44 and 45, respectively.
Figure 13:
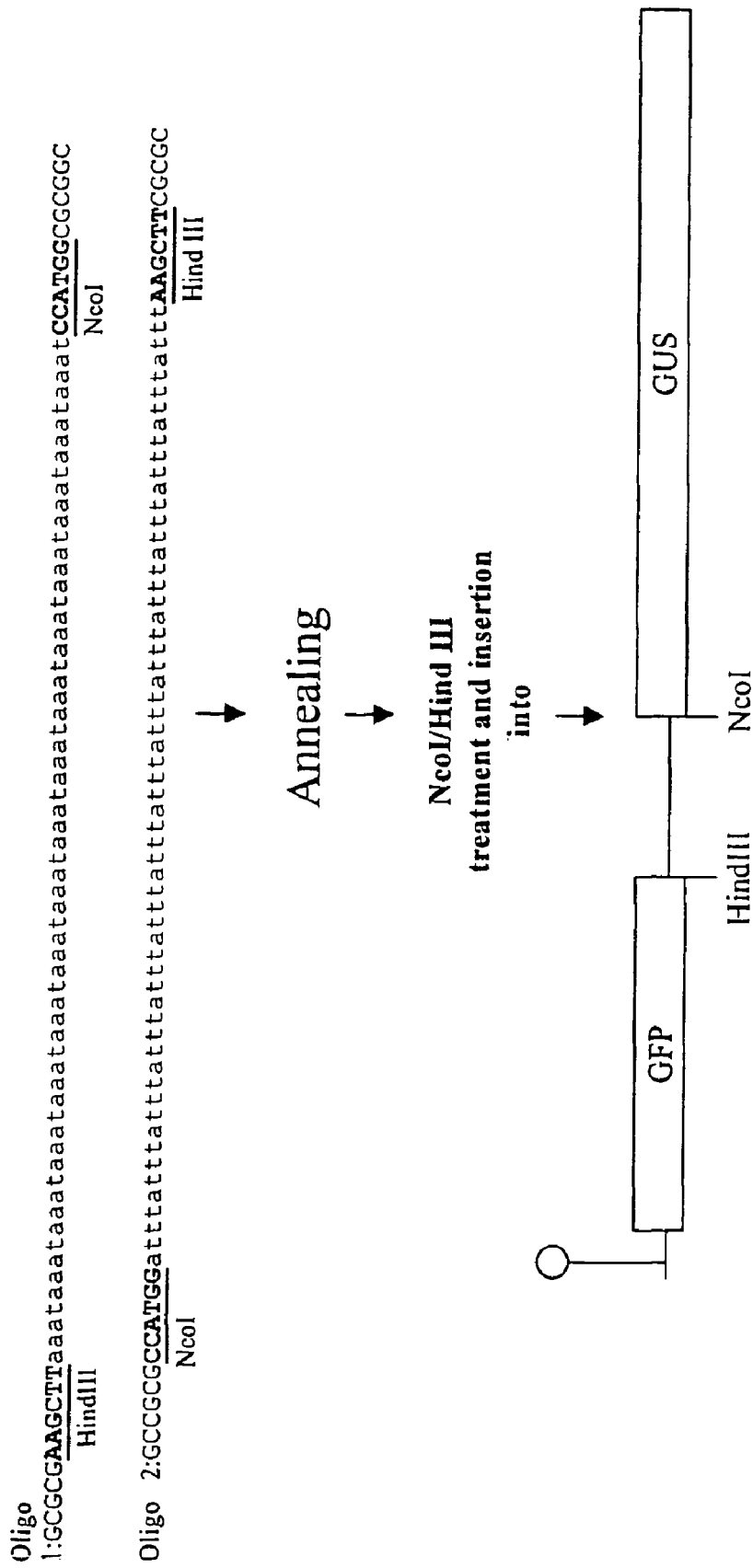
FIG. 13 depicts nucleotide primer sequences and cloning steps of an artificial IRES containing 16 copies of the AAAU element. Restriction sites are underlined. Oligos 1 and 2 correspond to SEQ ID NOS:46 and 47, respectively.
Figure 14:
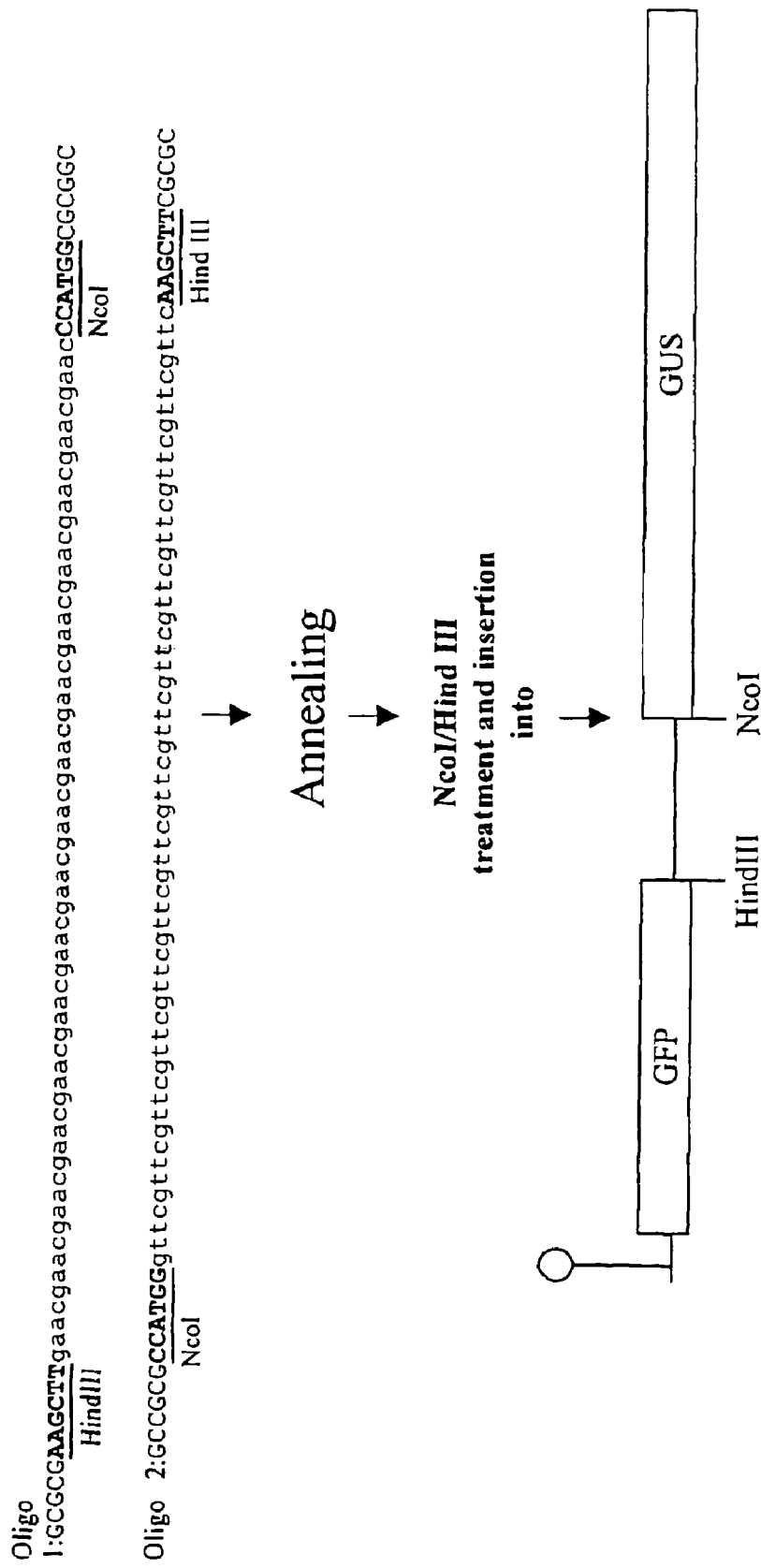
FIG. 14 depicts nucleotide primer sequences and cloning steps of an artificial IRES containing 16 copies of the GAAC element. Restriction sites are underlined. Oligos 1 and 2 correspond to SEQ ID NOS:48 and 49, respectively.
Figure 15:
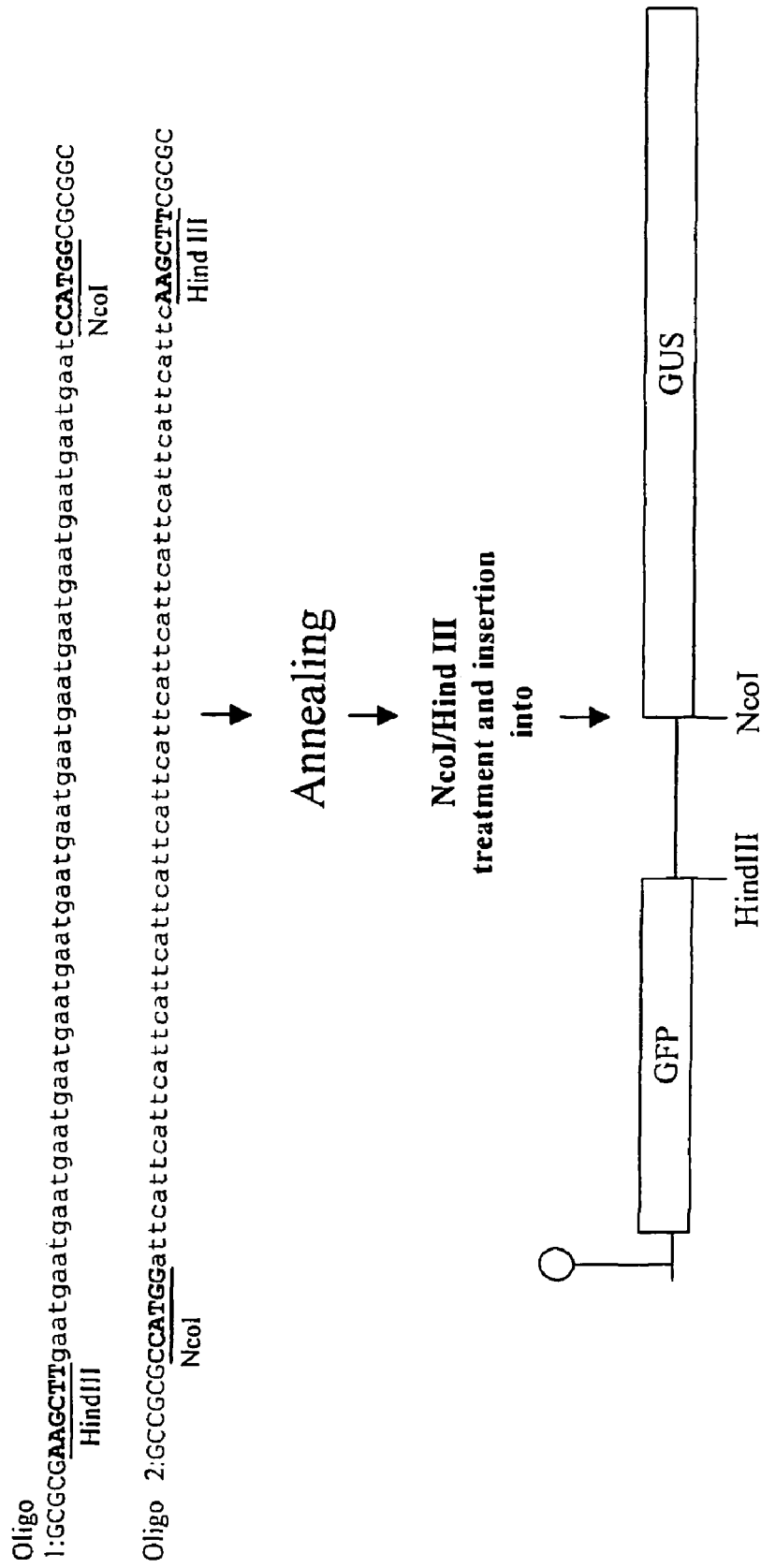
FIG. 15 depicts nucleotide primer sequences and cloning steps of an artificial IRES containing 16 copies of GAAU element. Restriction sites are underlined. Oligos 1 and 2 correspond to SEQ ID NOS:50 and 51, respectively.
Figure 16:
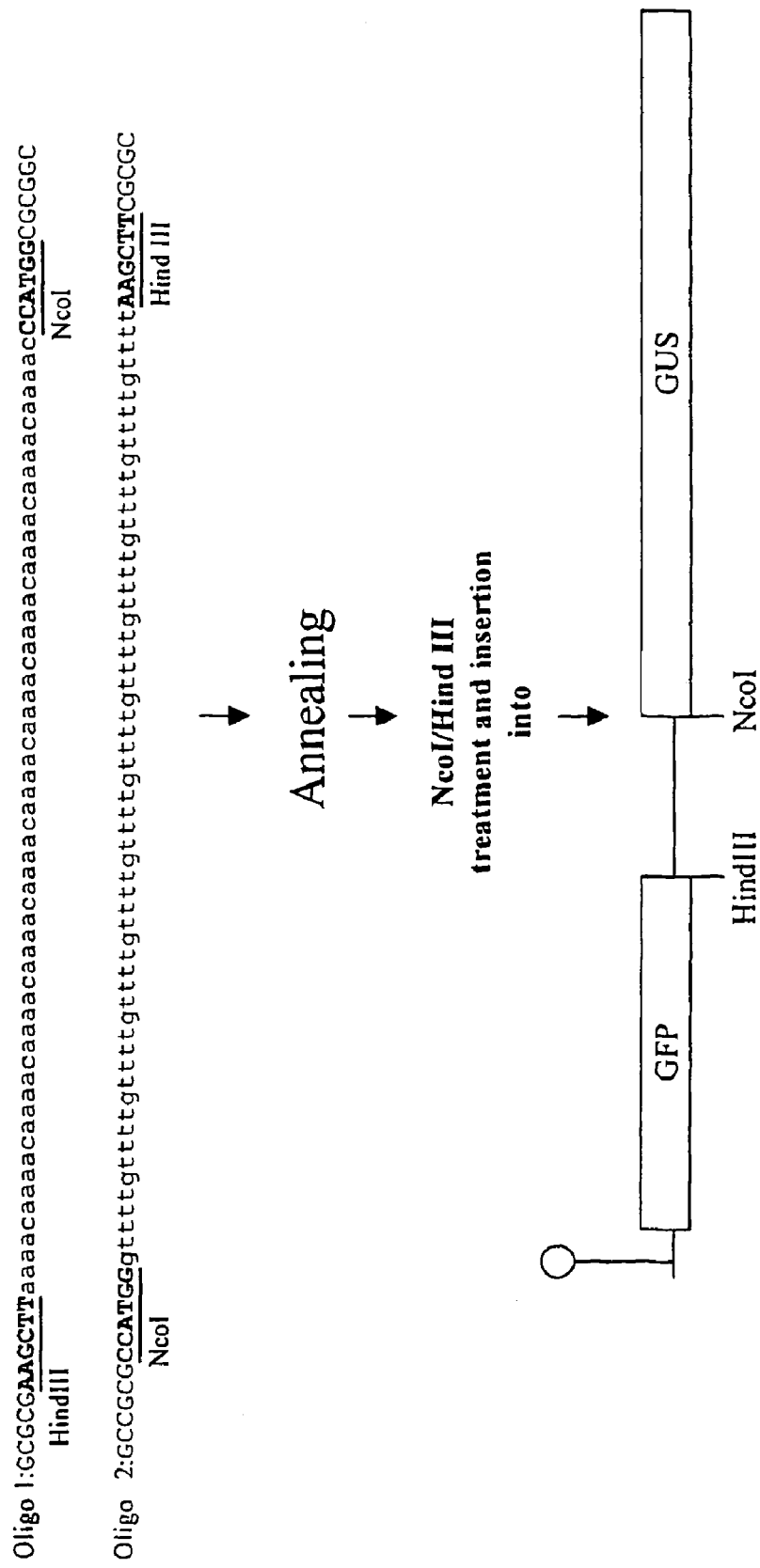
FIG. 16 depicts nucleotide primer sequences and cloning steps of artificial IRES containing 12 copies of the AAAAC element. Restriction sites are underlined. Oligos 1 and 2 correspond to SEQ ID NOS:52 and 53, respectively.
Figure 17:
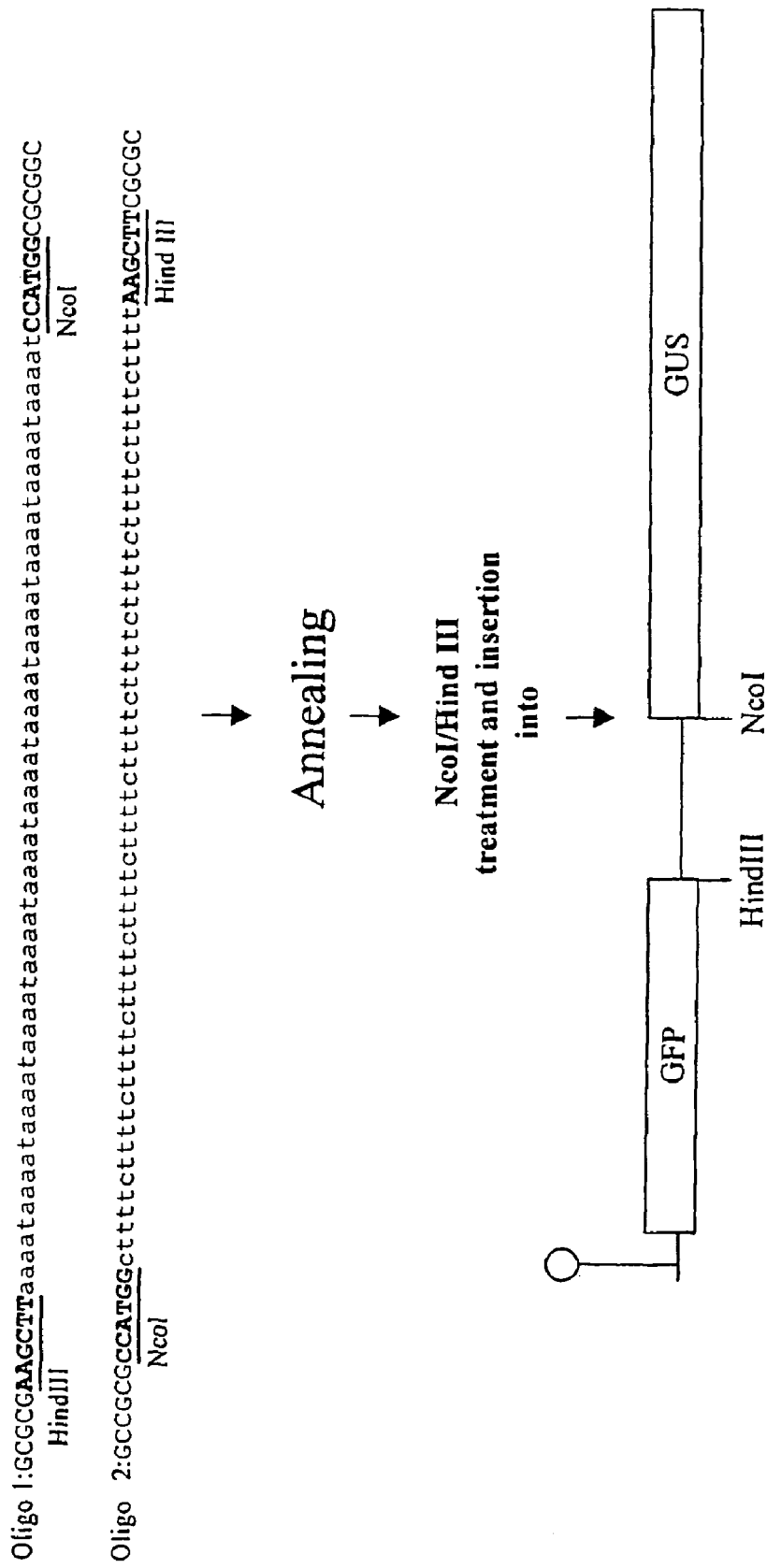
FIG. 17 depicts nucleotide primer sequences and cloning steps of artificial IRES containing 12 copies of the AAAAU element. Restriction sites are underlined. Oligos 1 and 2 correspond to SEQ ID NOS:54 and 55, respectively.
Figure 18:
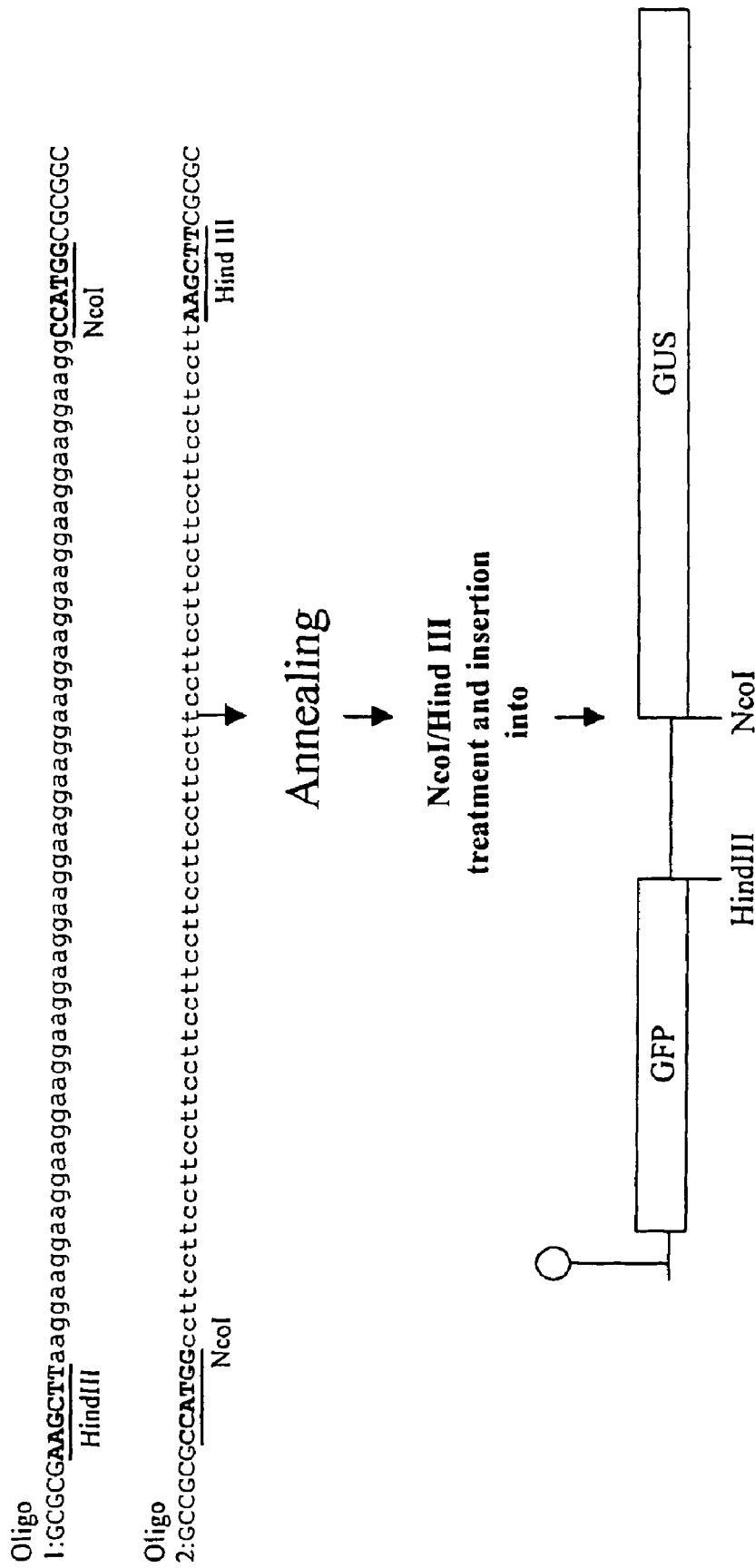
FIG. 18 depicts nucleotide primer sequences and cloning steps of an artificial IRES containing 16 copies of AAGG element. Restriction sites are underlined. Oligos 1 and 2 correspond to SEQ ID NOS:56 and 57, respectively.
Figure 19:
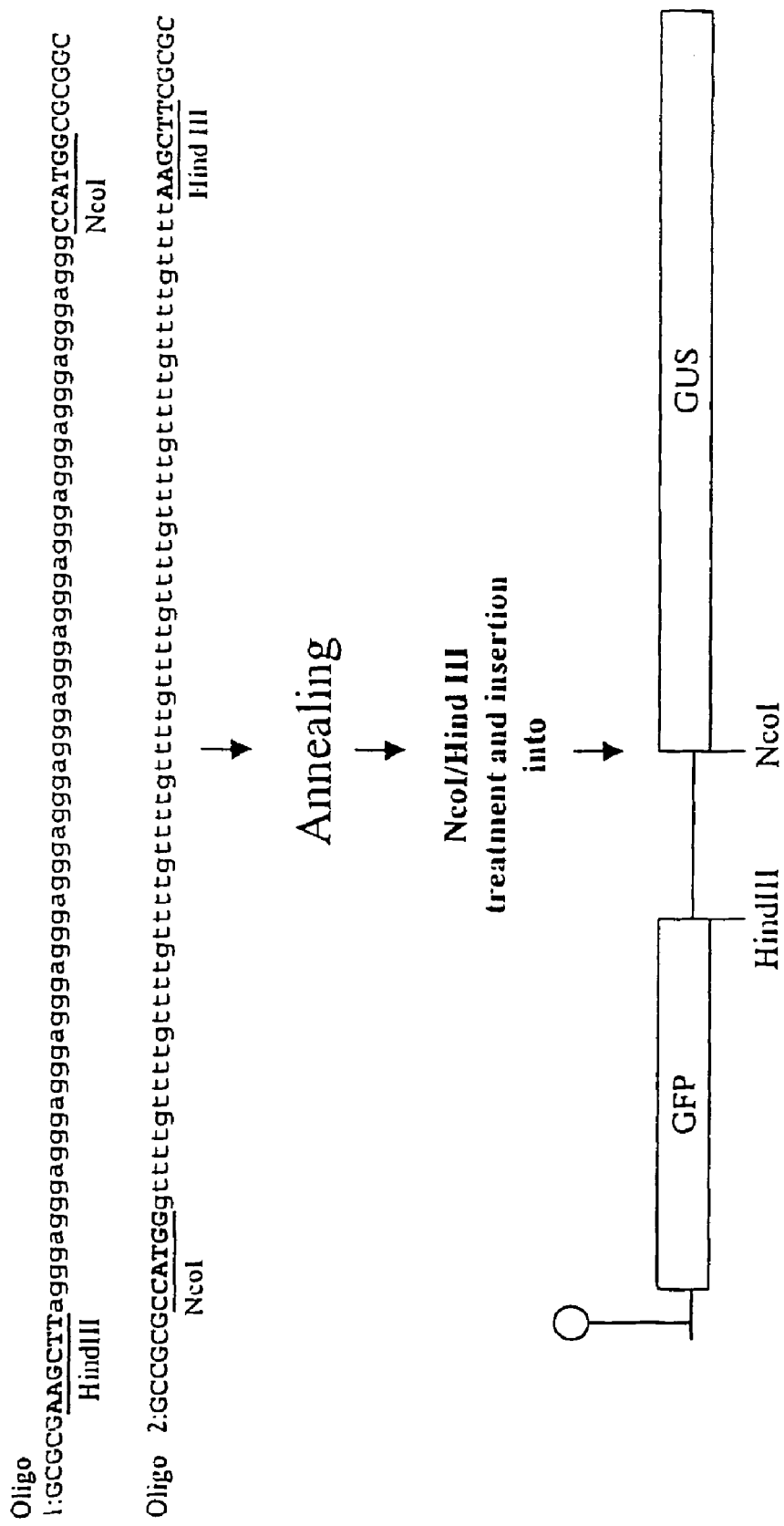
FIG. 19 depicts nucleotide primer sequences and cloning steps of artificial RES containing 16 copies of AGGG element. Restriction sites are underlined. Oligos 1 and 2 correspond to SEQ ID NOS:58 and 59, respectively.

Cloning Strategy:

Nucleotide primer sequences and cloning steps of artificial IRESes containing 16 copies of the AAAC and of the AAAU fragment, whereby the pyrimidine nucleotide content is 25% are presented in FIGS. 12 and 13, respectively. Nucleotide primer sequences and cloning steps of artificial IRESes containing 16 copies of the GAAC and of the GAAU fragment, whereby the guanine content is 25%, the adenosine content is 50% and the pyrimidine nucleotide content is 25% are presented in FIGS. 14 and 15, respectively. The next two examples of IRES elements having multiple copies of the AAAAC and of the AAAAU fragment demonstrate that the a pyrimidine nucleotide content of 20% does not abolish the IRES activity. The cloning strategy of these constructs is depicted in FIGS. 16 and 17, respectively. Two other artificial IRESes containing multiple copies of the AAGG (FIG. 18) and the AGGG (FIG. 19) fragment were built with the aim to determine the minimal adenine nucleotide content in a nucleotide block providing artificial IRES activity.

Results

We have created a series of synthetic sequences (FIGS. 5-9) which were used as intercistronic spacers in the bicistronic H-GFP-GUS vector and were examined in RRL, tobacco protoplasts and HeLa cells. Two synthetic sequences representing four linked copies of a 19-nt direct repeat (Ecp x4) and 16 copies of the GAAA sequence (GAAA)$_{16}$ (SEQ ID NO:63, FIGS. 5 and 6) were compared with two other types of artificial sequences: (i) GUUU-rich sequences (GUUU)$_{16}$ (SEQ ID NO:64, FIG. 7) and Emp x 4 (FIG. 8) and (ii) a GC-rich tetramer (GCRT) containing four copies of the 8-nt GC-rich sequence CGCGGGCG linked by the 6-nt sequence UUUGUUU (FIG. 9).

Figure 20:
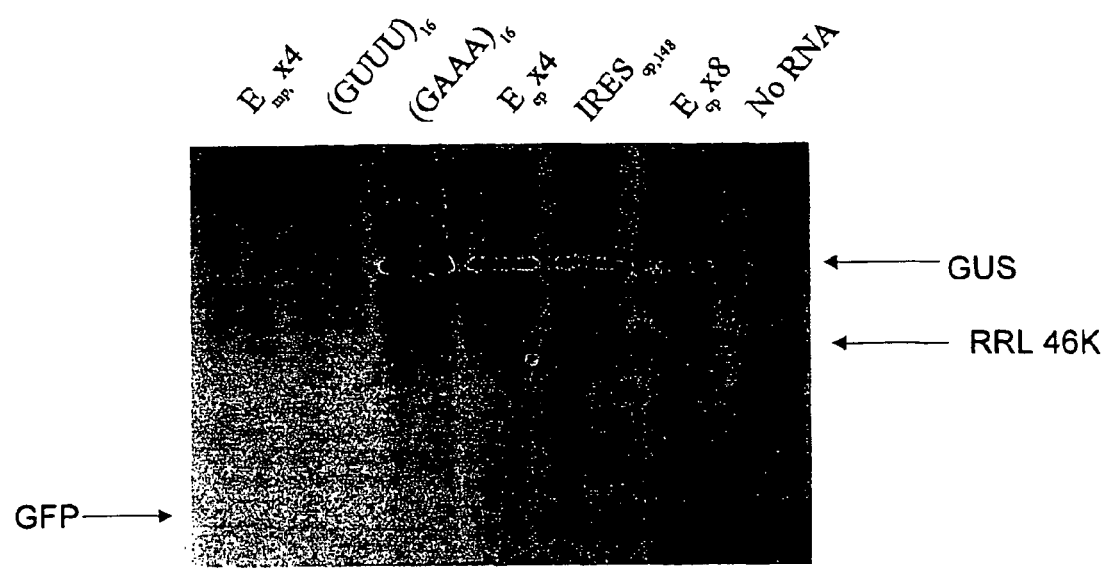
FIG. 20 shows an autoradiograph of proteins translated in RRL by H-GFP-GUS containing artificial sequences as intercistronic spacers. Arrows indicate the position of GUS and expected positions of endogenic RRL 46K protein and GFP.

RRL translation of bicistronic H-GFP-GUS containing artificial sequences as intercistronic spacers showed (FIG. 20) that the artificial sequences Ecp x4 and (GAAA)$_{16}$ (SEQ ID NO:63), efficiently directed GUS gene translation under conditions when GFP gene translation was blocked by stable hairpin (H) structure. Moreover, in vitro efficiency of these two sequences was even higher than the natural IRES$_{CP,148}^{CR}$, whereas lengthening of Ecp x4 to 8 copies (Ecp x8) did not increase GUS gene expression. The GUUU-rich sequences Emp x4 and (GUUU)$_{16}$, (SEQ ID NO:64) turned out to have a negligible effect on GUS synthesis (FIG. 20). The GCRT sequence did not have IRES activity neither (data not shown).

Figure 21:
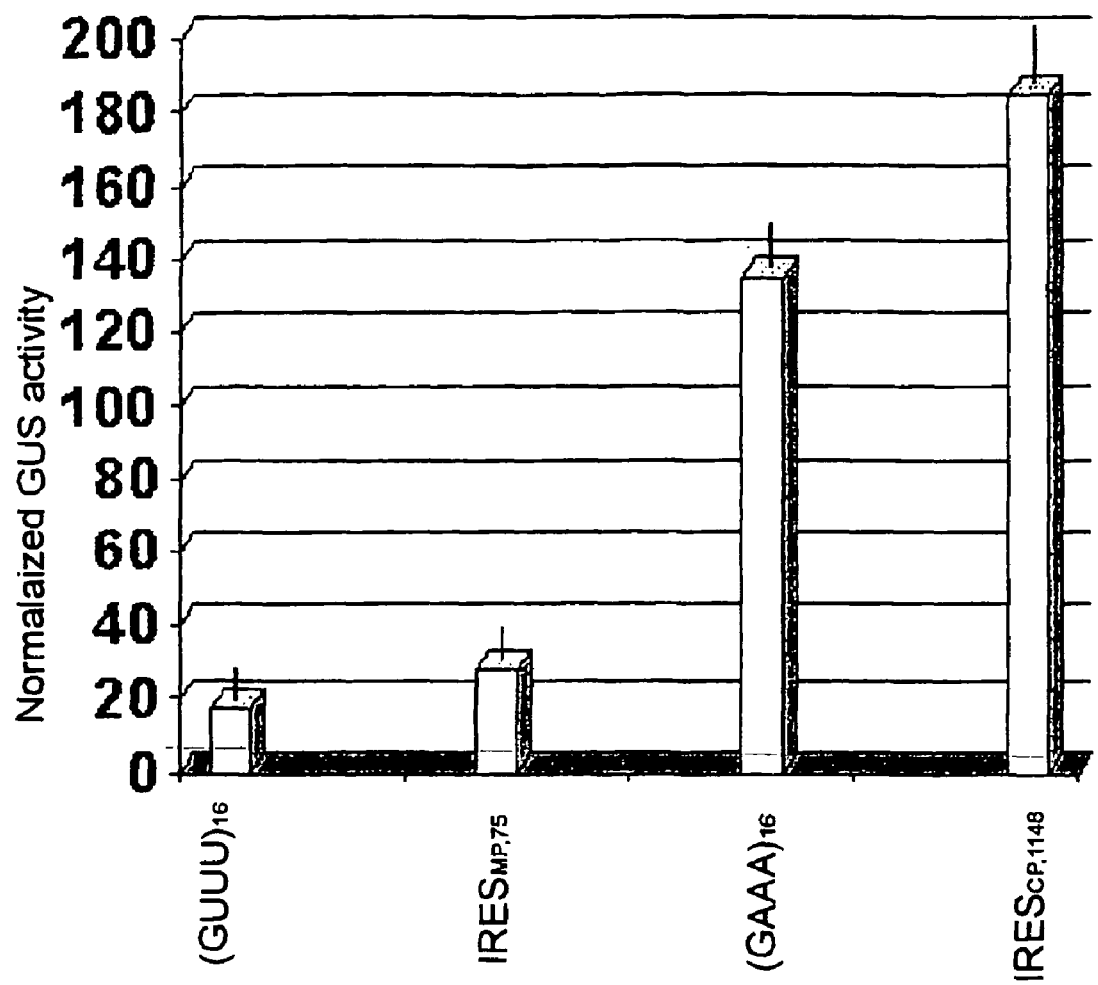
FIG. 21 shows a diagram of GUS gene expression in tobacco protoplast cells transfected with 35 S-based bicistronic GFP-GUS constructs lacking a hairpin and containing nucleotide sequences as indicated under the diagram bars. The GUS activity values of each sample were normalized to the GFP content in the same protoplast sample determined by densitometry of GFP bands from Western blots. At least three independent experiments were used for the calculation of average values and standard errors.
Figure 22:
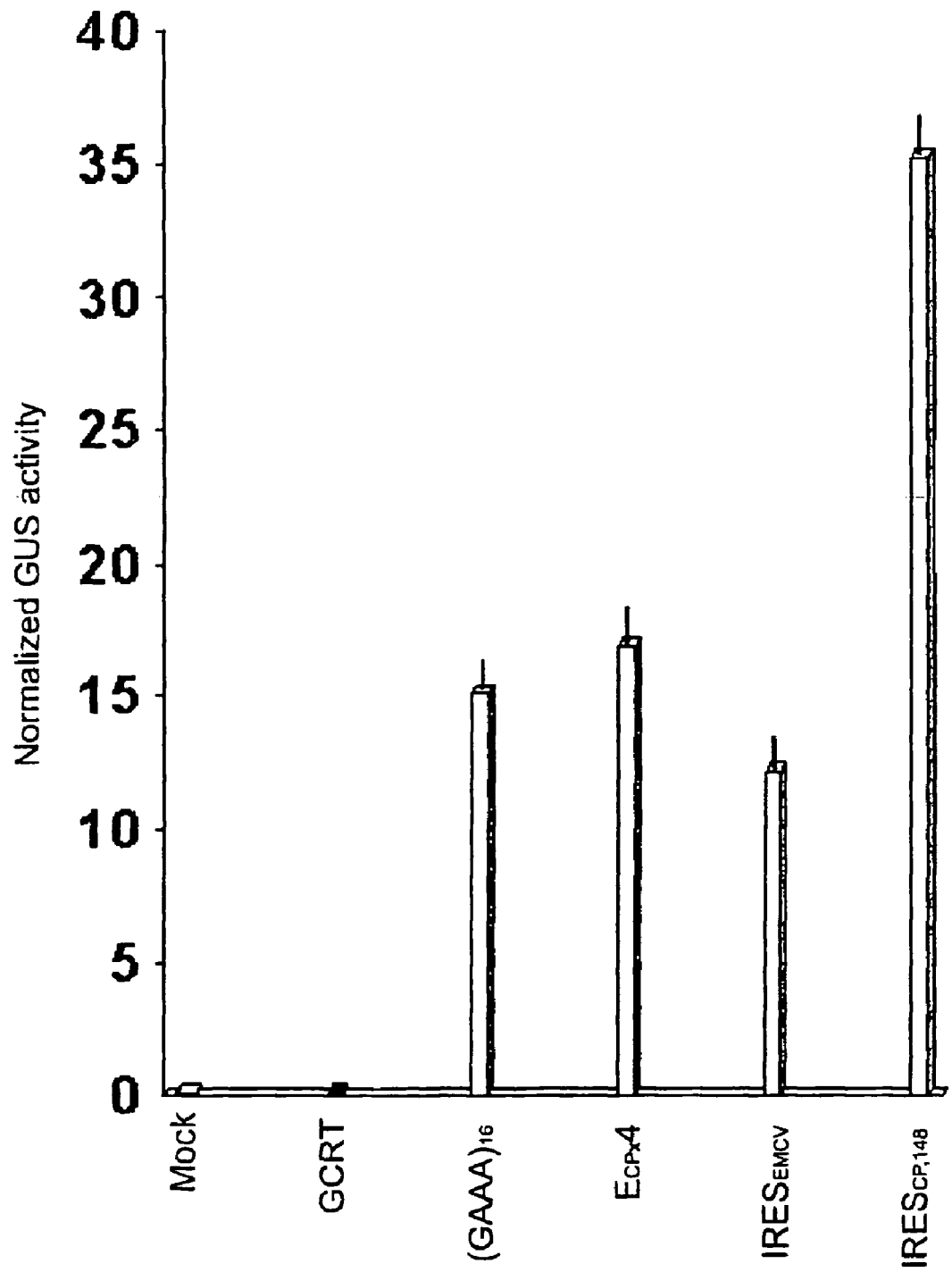
FIG. 22 shows a diagram of GUS gene expression in HeLa cells transfected with bicistronic T7-based H-GFP-GUS transcripts. GUS measurement were conducted as described in the Examples and were normalised to the protein contents of the samples. At least three independent experiments were used for the calculation of average values and standard errors.

In vivo experiments on tobacco protoplasts (FIG. 21) and HeLa cells (FIG. 22) transfected with H-GFP-GUS constructs containing the artificial sequences as described above, confirmed the in vitro results: the artificial sequence (GAAA)$_{16}$ (SEQ ID NO:63) was able to function as an IRES element even more efficiently than IRES$^{EMCV}$ (in HeLa cells) and comparably to IRES$_{CP,148}^{CR}$ (protoplasts and HeLa cells).

Results with artificial sequences containing poly(A) and poly(G) sequences demonstrated that in contrast to the poly(G) sequence, the artificial IRES based on 100% content of adenine functions efficiently as an IRES (Table 1).

TABLE 1

GUS expression in RRL directed by poly(A) and poly(G) sequences used as intercistronic spacers of bicistronic H-GFP-GUS transcripts. Samples were incubated at 30° C. for 60 min. GUS activity was measured in 2 µl aliquots using MUG.

| Construct | 4 MU fluoresc. after 30' (RLU) | 4 MU fluoresc. after 30' (RLU) |
|---|---|---|
| hGFP-PolyA-GUS | 313497 | 490197 |
| hGFP-PolyG-GUS | 625 | 659 |
| hGFP-IRES$_{CP}$148-GUS | 208499 | 358621 |
| No RNA | 643 | 674 |

The invention claimed is:

1. An isolated transgenic or transiently modified cell comprising an expression cassette comprising a first nucleotide sequence of interest to be expressed, said first nucleotide sequence of interest being operably linked to an upstream second nucleotide sequence, the second nucleotide sequence comprising an IRES element that directs cap-independent translation of said first nucleotide sequence wherein said IRES element is an adenine-rich nucleic acid block of at least 25 nucleotides in length, said adenine-rich nucleic acid block comprising at least 90% content adenine.

2. The isolated transgenic or transiently modified cell according to claim 1, wherein said first nucleotide sequence encodes a reporter protein.

3. The isolated transgenic or transiently modified cell according to claim 1, wherein said cell is a plant cell or a protoplast thereof.

4. The isolated transgenic or transiently modified cell according to claim 1, wherein said cell is an animal cell.

5. The isolated transgenic or transiently modified cell according to claim 4, wherein said cell is a human cell.

6. The isolated transgenic or transiently modified cell according to claim 1, wherein said cell is a fungal cell.

7. The isolated transgenic or transiently modified cell according to claim 6, wherein said cell is a yeast cell.

8. The isolated transgenic or transiently modified cell of claim 1, wherein said adenine-rich nucleic acid block is at least 40 nucleotides in length.

9. A process of expressing a nucleotide sequence of interest in a cell, comprising introducing into the cell an expression cassette comprising a first nucleotide sequence of interest to be expressed, said first nucleotide sequence of interest being operably linked to an upstream second nucleotide sequence, the second nucleotide sequence comprising an IRES element that directs cap-independent translation of said first nucleotide sequence wherein said IRES element is an adenine-rich nucleic acid block of at least 25 nucleotides in length, said adenine-rich nucleic acid block comprising at least 90-% content adenine.

10. The process according to claim 9, wherein said first nucleotide sequence of interest is expressed from a bicistronic or polycistronic mRNA.

11. The process according to claim 9, wherein said cell is selected from the group consisting of a plant cell, an animal cell, and a yeast cell.

12. The process according to claim 9, wherein said adenine-rich nucleic acid block is a poly(A) element.

13. A non-human eukaryotic organism comprising a cell comprising an expression cassette comprising a first nucleotide sequence of interest to be expressed, said first nucleotide sequence of interest being operably linked to an upstream second nucleotide sequence, the second nucleotide sequence comprising an IRES element that directs cap-independent translation of said first nucleotide sequence wherein said IRES element is an adenine-rich nucleic acid block of at least 25 nucleotides in length, said adenine-rich nucleic acid block comprising at least 90% content adenine.

14. The organism of claim 13, wherein said organism is a plant.

* * * * *